US006524249B2

(12) United States Patent
Moehring et al.

(10) Patent No.: US 6,524,249 B2
(45) Date of Patent: Feb. 25, 2003

(54) DOPPLER ULTRASOUND METHOD AND APPARATUS FOR MONITORING BLOOD FLOW AND DETECTING EMBOLI

(75) Inventors: Mark A. Moehring, Seattle, WA (US); Timothy R. Myers, Snohomish, WA (US)

(73) Assignee: Spentech, Inc., Seattle, WA (US)

( * ) Notice: Subject to any disclaimer, the term of this patent is extended or adjusted under 35 U.S.C. 154(b) by 26 days.

(21) Appl. No.: 09/731,645

(22) Filed: Dec. 6, 2000

(65) Prior Publication Data

US 2002/0091319 A1 Jul. 11, 2002

Related U.S. Application Data

(63) Continuation-in-part of application No. 09/190,402, filed on Nov. 11, 1998, now Pat. No. 6,196,972.

(51) Int. Cl.[7] .................................................. A61B 8/06
(52) U.S. Cl. ........................................ 600/438; 600/454
(58) Field of Search .......................... 600/438, 453–456; 604/4, 50; 364/421–424

(56) References Cited

U.S. PATENT DOCUMENTS

| 4,014,206 A | | 3/1977 | Taylor ............................ 73/19 |
| 4,152,928 A | * | 5/1979 | Roberts ..................... 73/194 A |
| 4,319,580 A | * | 3/1982 | Colley et al. ................. 600/467 |
| 4,501,277 A | | 2/1985 | Hongo ......................... 600/441 |
| 4,848,354 A | | 7/1989 | Angelsen et al. ......... 128/660.05 |
| 5,053,008 A | * | 10/1991 | Bajaj ........................... 604/104 |
| 5,103,826 A | | 4/1992 | Bonnefous ................... 600/454 |
| 5,103,827 A | * | 4/1992 | Smith ........................... 600/454 |
| 5,148,808 A | | 9/1992 | Satake .................... 128/660.05 |
| 5,271,404 A | | 12/1993 | Corl et al. ............... 128/661.08 |
| 5,348,015 A | * | 9/1994 | Moehring et al. ....... 364/413.02 |
| 5,441,051 A | | 8/1995 | Hileman et al. ......... 128/661.08 |
| 5,476,097 A | | 12/1995 | Robinson .............. 128/660.05 |
| 5,501,223 A | | 3/1996 | Washburn et al. ..... 128/661.09 |

(List continued on next page.)

FOREIGN PATENT DOCUMENTS

| EP | 0 079 453 A1 | 5/1983 |
| WO | WO 94/06353 | 3/1994 |

OTHER PUBLICATIONS

Kremkau, G. W. *Doppler Ultrasound, Principles and Instruments.* (Philadelphia, W.B. Saunders Company, 1990), pp. 177–211.

Omoto, R. et al., "The Development of Real–Time Two–Dimensional Doppler Echocardiography and Its Clinical Significance in Acquired Valvular Diseases With Special Reference to the Evaluation of Valvular Regurgitation", Reprinted from *Japanese Heart Journal*, vol. 25, No. 3, pp. 325–340, May, 1984.

(List continued on next page.)

*Primary Examiner*—Francis J. Jaworski
(74) *Attorney, Agent, or Firm*—Dorsey & Whitney LLP

(57) ABSTRACT

A pulse Doppler ultrasound system and associated methods are described for monitoring blood flow and detecting emboli. A graphical information display includes simultaneously displayed depth-mode and spectrogram displays. The depth-mode display indicates the various positions along the ultrasound beam axis at which blood flow is detected. These positions are indicated as one or more colored regions, with the color indicating direction of blood flow and varying in intensity as a function of detected Doppler ultrasound signal amplitude or detected blood flow velocity. The depth-mode display also includes a pointer whose position may be selected by a user. The spectrogram displayed corresponds to the location identified by the pointer. Embolus detection is also provided.

97 Claims, 15 Drawing Sheets

(2 of 15 Drawing Sheet(s) Filed in Color)

U.S. PATENT DOCUMENTS

| | | | | |
|---|---|---|---|---|
| 5,622,173 | A | 4/1997 | Bisson et al. | 128/661.01 |
| 5,785,655 | A | 7/1998 | Goodsell, Jr. et al. | 600/441 |
| 5,882,315 | A | 3/1999 | Ji et al. | 600/553 |
| 5,919,139 | A | 7/1999 | Lin | 600/443 |
| 5,997,478 | A | 12/1999 | Jackson et al. | 600/437 |
| 6,045,505 | A | 4/2000 | Holley et al. | 600/441 |
| 6,196,972 | B1 * | 3/2001 | Moehring | 600/454 |

OTHER PUBLICATIONS

Omoto, R., et al., Clinical Significance and Prospects of 'Real–Time Two–Dimensional Doppler Echocardiography', Color Atlas of Real–Time Two–Dimensional Doppler Echocardiography, Chapters 1–6, pp. 1–44, Shindan –To–Chiryo Co., Ltd. Tokyo 1984.

*Aloka–860 Operational Manual.* Vol. I System Description, Effective S/N: 51M8876 and above. pp. i—15–2 and A–2—A–5.

*Aloka Color Doppler Model SSD–860 Cardiovascular Scanner* Sales Brochure. Aloka Co., Ltd., Japan.

Duncan, W. J. *Color Doppler in Clinical Cardiology.* Philadelphia, W.B. Saunders Company, Harcourt Brace Jovanovich, Inc., 1988. pp. 1–13.

Iwase, M. et al. *Clinical Echocardiography.* Dordrecht, Kluwer Academic Publishers, 1989. pp. 11–27 and 250–281.

Missri, J. *Clinical Doppler Echocardiography Spectral and Color Flow Imaging.* New York, McGraw–Hill, Inc., 1990. pp. 9–27 and 279–303.

Redel, D. A. *Color Blood Flow Imaging of the Heart.* Germany, Springer–Verlag Berlin Heidelberg, 1988. pp. 5–12 and 27–41.

Weyman, A. E. *Principles and Practice of Echocardiography*, 2d ed. Philadelphia, Lea & Febiger, 1994. pp. 218–233 and 256–281.

* cited by examiner

EMBOLUS CHARACTERIZATION SUBROUTINE

DOPPLER ULTRASOUND METHOD AND APPARATUS FOR MONITORING BLOOD FLOW AND DETECTING EMBOLI

CROSS-REFERENCE TO RELATED APPLICATION

This application is a continuation-in-part of U.S. patent application Ser. No. 09/190,402, filed Nov. 11, 1998, now U.S. Pat. No. 6,156,972.

STATEMENT AS TO GOVERNMENT RIGHTS

This invention was made with United States Government support under Grant No. 2 R44 HL 57108-02 awarded by National Institutes of Health (NIH). The United States Government has certain rights in the invention.

TECHNICAL FIELD

The invention relates generally to medical monitoring and diagnostic procedures and devices, and more particularly to a Doppler ultrasound method and apparatus for monitoring blood flow.

BACKGROUND OF THE INVENTION

Doppler ultrasound has been used to measure blood flow velocity for many years. The well-known Doppler shift phenomenon provides that ultrasonic signals reflected from moving targets will have a shift in frequency directly proportional to the target velocity component parallel to the direction of the ultrasound beam. The frequency shift is the same for any object moving at a given velocity, whereas the amplitude of the detected signal is a function of the acoustic reflectivity of the moving object reflecting the ultrasound. Pulse Doppler ultrasound systems commonly produce a spectrogram of the detected return signal frequency (i.e., velocity) as a function of time in a particular sample volume, with the spectrogram being used by a physician to determine blood flow characteristics of a patient.

Some Doppler ultrasound systems also have the capability to detect and characterize emboli flowing in the bloodstream. An example Doppler ultrasound system with embolus detection capability is described in U.S. Pat. No. 5,348,015, entitled "Method And Apparatus For Ultrasonically Detecting, Counting, and/or Characterizing Emboli," issued Sep. 20, 1994, to Moehring et al., the disclosure of which is incorporated herein by reference. Such ultrasound systems are advantageously used both for diagnostic exams (to determine the presence and significance of vascular disease or dysfunction) and during surgical interventions (to indicate surgical manipulations that produce emboli or alter/interrupt blood flow).

Typically, a user of ultrasound equipment finds it rather difficult to properly orient and position an ultrasound transducer or probe on the patient, as well as to select a depth along the ultrasound beam corresponding to the desired location where blood flow is to be monitored. This is particularly true in ultrasound applications such as transcranial Doppler imaging (TCD). The blood vessels most commonly observed with TCD are the middle, anterior, and posterior cerebral arteries, and the vertebral and basilar arteries. The Doppler transducer must be positioned so the ultrasound beam passes through the skull via the temporal windows for the cerebral arteries, and via the foramen magnum for the vertebral and basilar arteries. The user of the ultrasound equipment may find it difficult to locate these particular windows or to properly orient the ultrasound probe once the particular window is found.

A complicating factor in locating the ultrasound window is determination of the proper depth at which the desired blood flow is located. Commonly, the user does not know if he is looking in the correct direction at the wrong depth, the wrong direction at the right depth, or whether the ultrasound window is too poor for appreciating blood flow at all. Proper location and orientation of the Doppler ultrasound probe, and the proper setting of depth parameters, is typically by trial and error. Not only does this make the use of Doppler ultrasound equipment quite inconvenient and difficult, it also creates a risk that the desired sample volume may not be properly located, with the corresponding diagnosis then being untenable or potentially improper.

Moreover, although some Doppler ultrasound systems have the ability to detect and characterize emboli flowing in the blood stream, these systems have relatively limited detection capability. Typically, conventional Doppler ultrasound systems rely on the Doppler signature sampled in one or two closely spaced sample gate positions and are limited to detection at only these gate positions. Consequently, distinguishing embolic signals from artifact signals and accurately locating emboli using conventional Doppler ultrasound systems proves to be a difficult task.

SUMMARY OF THE INVENTION

In accordance with the invention, an information display is provided in connection with Doppler ultrasound monitoring of blood flow. The information display includes two simultaneously displayed graphical displays. One graphical display is a blood locator display that indicates locations along the axis of the ultrasound beam at which blood flow is detected. The blood locator display includes a location indicator, such as a pointer directed to a selected one of the locations. The other graphical display is a spectrogram indicating velocities of monitored blood flow at the selected location. The blood locator display may include a color region corresponding with the locations at which blood flow is detected. The intensity of the color may vary as a function of detected ultrasound signal amplitude or as a function of detected blood flow velocities.

The blood locator display allows a user to quickly locate blood flow along the ultrasound beam axis. Using the blood locator display, the location of blood flow of particular interest can be further refined by the user adjusting the aim of the ultrasound probe to produce a greater displayed intensity or spatial extent at the particular location of interest. The user may then select the position of the pointer to view the corresponding spectrogram. The user may also use the two simultaneously displayed graphical displays to locate a particular blood vessel by detecting temporal or other variations in the displays that are consistent with the blood vessel.

A method for detecting embolic events comprised of various algorithm parts is included. The detection method may include less than all of the algorithm parts for effective embolus detection. The algorithm parts include subtracting a respective background power level from compiled detected Doppler ultrasound power for each of a plurality of time periods and locations along the ultrasound beam axis, removing from the subtracted compiled movement information movement information having a detected velocity less than a velocity threshold, performing a plurality of binary characterization tests to determine whether the resultant compiled movement information is consistent with the occurrence of an embolic event, and reviewing the results of the binary characterization tests and identifying false positive identification of embolic events. Embolus detection may also be made by visual observation of the compiled movement information.

DETAILED DESCRIPTION OF THE INVENTION

The following describes a novel method and apparatus for providing Doppler ultrasound information to a user, such as in connection with measuring blood velocities to detect hemodynamically significant deviations from normal values, and to assess blood flow for the occurrence of microembolic signals. Certain details are set forth to provide a sufficient understanding of the invention. However, it will be clear to one skilled in the art that the invention may be practiced without these particular details. In other instances, well-known circuits, control signals, timing protocols, and software operations have not been shown in detail in order to avoid unnecessarily obscuring the invention.

Figure 1:
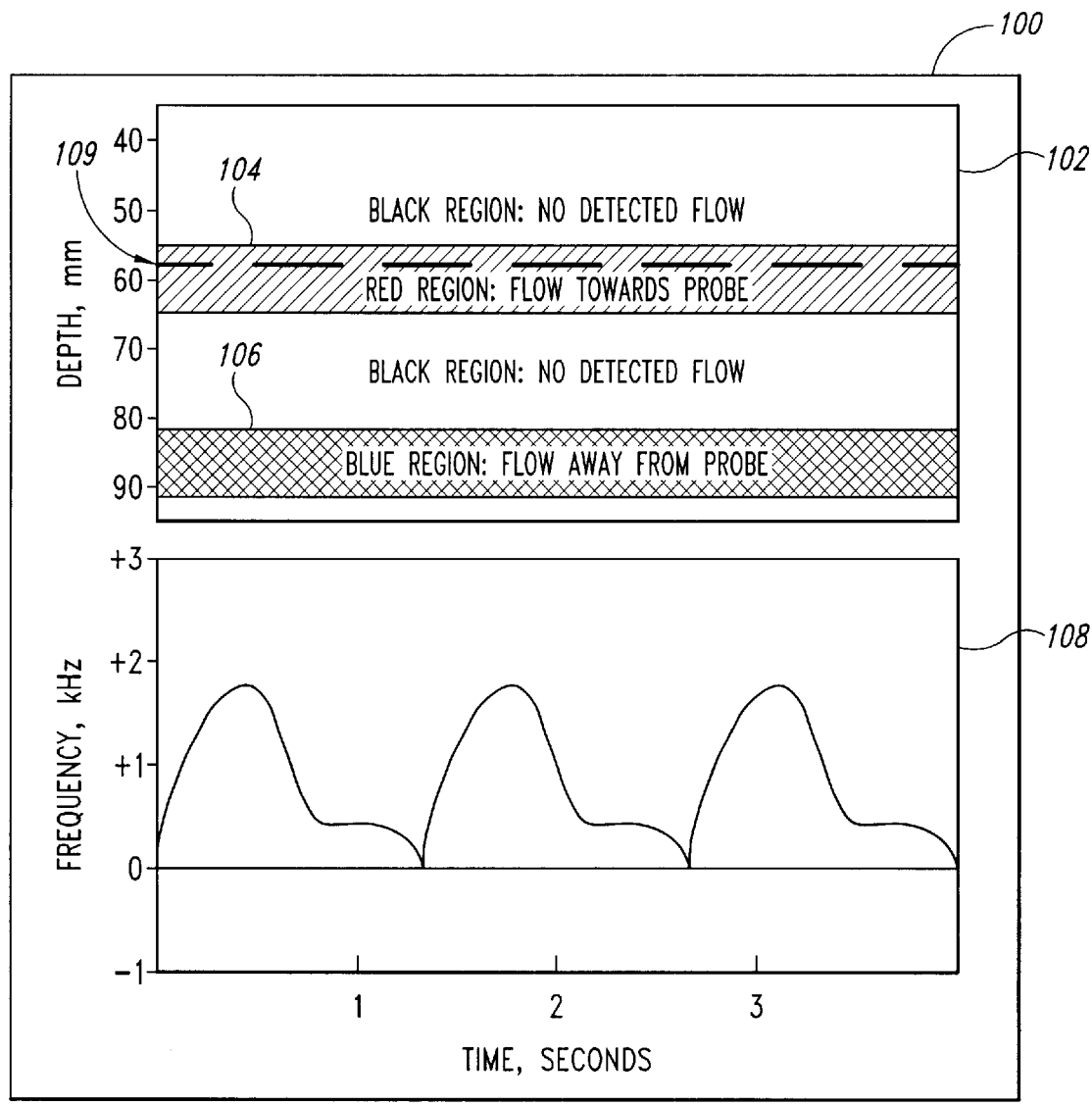
FIG. 1 is a graphical diagram depicting a first Doppler ultrasound system display mode in accordance with an embodiment of the invention.

FIG. 1 is a graphical diagram depicting a first display mode of Doppler ultrasound information in accordance with an embodiment of the invention. In this first display mode, referred to as an Aiming mode 100, two distinct ultrasound displays are provided to the user. A depth-mode display 102 depicts, with color, blood flow away from and towards the ultrasound probe at various depths along the ultrasound beam axis (vertical axis) as a function of time (horizontal axis).

The depth-mode display 102 includes colored regions 104 and 106. Region 104 is generally colored red and depicts blood flow having a velocity component directed towards the probe and in a specific depth range. Region 106 is generally colored blue and depicts blood flow having a velocity component away from the probe and in a specific depth range. The red and blue regions are not of uniform color, with the intensity of red varying as a function of the detected intensity of the return Doppler ultrasound signal. Those skilled in the art will understand that such a display is similar to the conventional color M-mode display, in which variation in red and blue coloration is associated with variation in detected blood flow velocities. However, such M-mode displays have not been used concurrently with a spectrogram and with the specific application of locating blood flow as an input to the spectrogram, from which diagnostic decisions are made.

The Aiming mode 100 also includes a displayed spectrogram 108, with FIG. 1 depicting a velocity envelope showing the characteristic systolic-diastolic pattern. Like the depth-mode display 102, the spectrogram 108 includes data points (not shown) within the velocity envelope that are colored in varying intensity as a function of the detected intensity of the return ultrasound signal. The particular sample volume for which the spectrogram 108 applies is at a depth indicated in the depth-mode display 102 by a depth indicator or pointer 109. In this way, a user of the ultrasound system can conveniently see and select particular depths at which to measure the spectrogram 108. The depth-mode display 102 readily and conveniently provides the information concerning the range of appropriate depths at which a meaningful spectrogram may be obtained.

Figure 2:
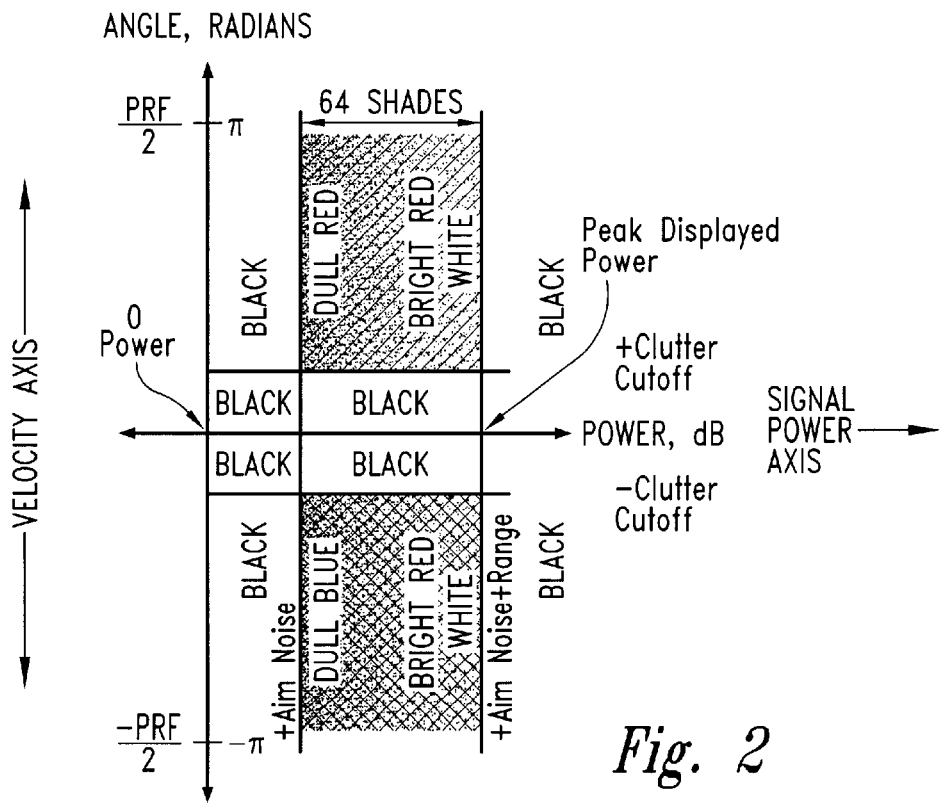
FIG. 2 is a graphical diagram depicting velocity and signal power parameters used in preparation of the display mode of FIG. 1.

As described above, the color intensity of regions 104 and 106 preferably vary as a function of the detected intensity of the return ultrasound signal. Referring to FIG. 2, a graphical diagram depicts how such color intensity is determined. In order to avoid display of spurious information, signals that may be intense but low velocity (such as due to tissue motion) are ignored and not displayed in the depth-mode display 102 of FIG. 1. This is referred to as clutter filtering and is depicted in FIG. 2 as the threshold magnitude clutter cutoff limits for positive and negative velocities. Similarly, low power signals associated with noise are also ignored and not displayed in the depth-mode display 102 of FIG. 1. The user can determine the upper power limit for the color intensity mapping by selecting a power range value. Signals above a maximum power are then ignored—another clutter filtering which is especially helpful when monitoring blood flow in the cardiac environment. Those skilled in the art will appreciate that other filtering techniques may be employed to improve the depth-mode display image, including delta modulator or other suitably adapted filtering techniques.

Figure 3:
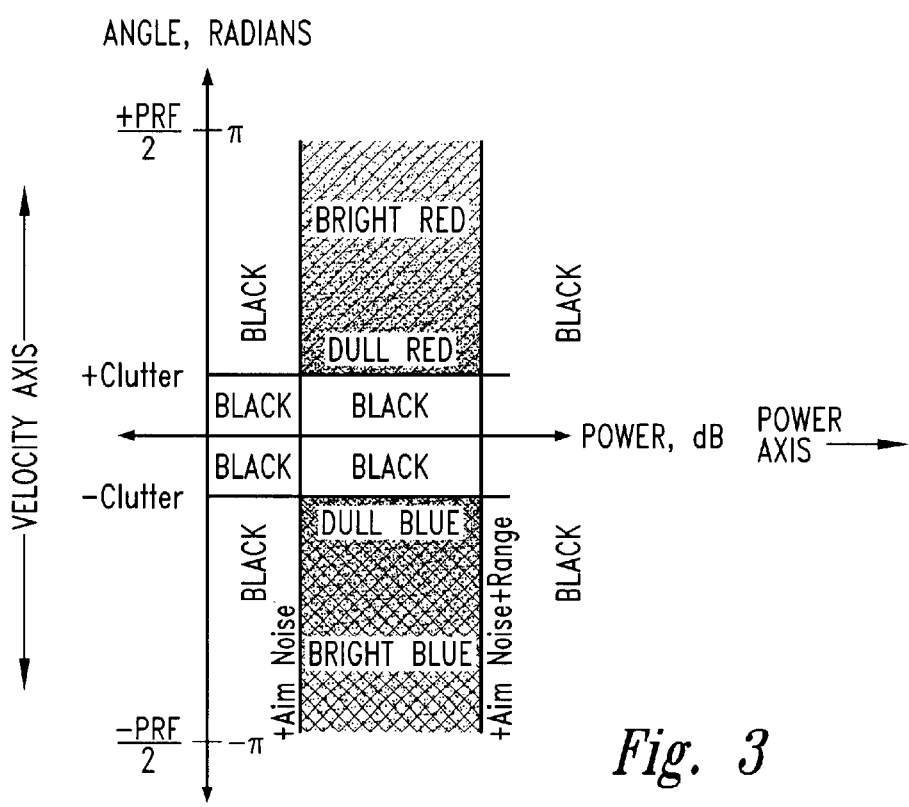
FIG. 3 is a graphical diagram depicting velocity and signal power parameters used in preparation of an alternative embodiment of the display mode of FIG. 1.
Figure 4:
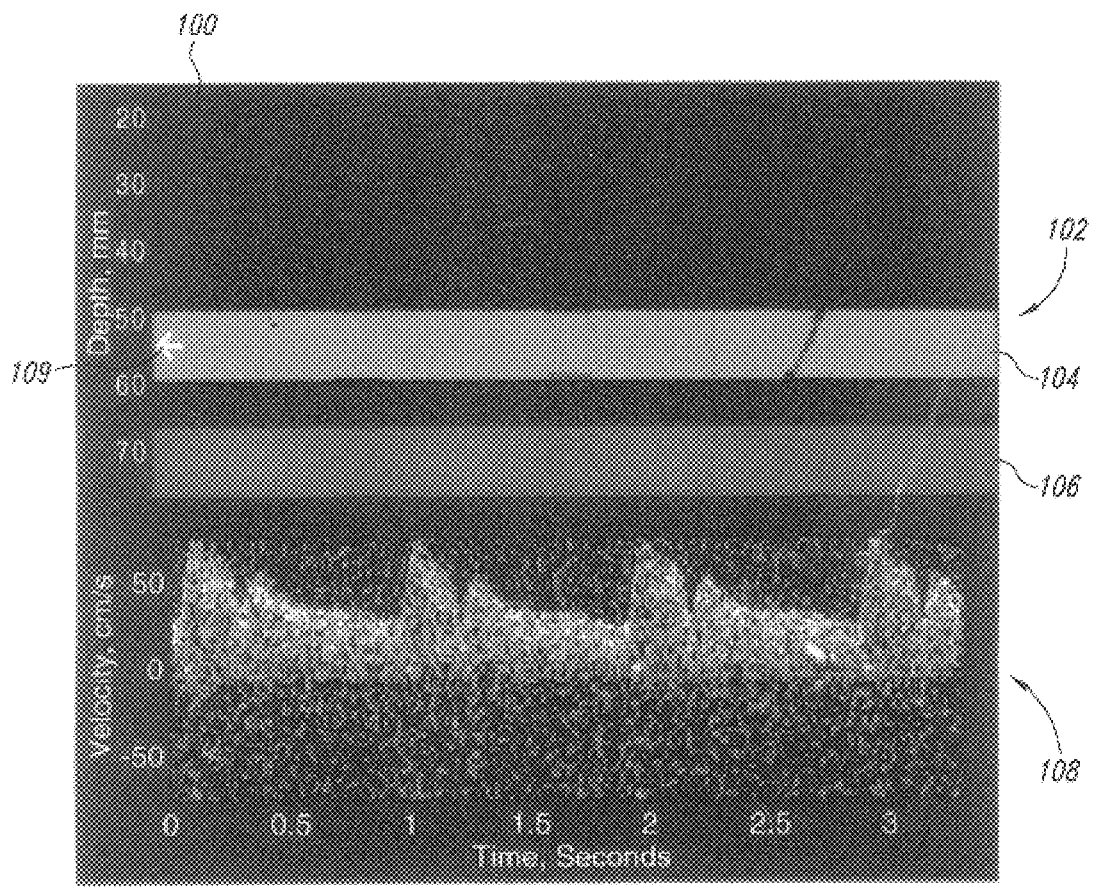
FIG. 4 shows the alternative embodiment of the display mode of FIG. 1 in color.

While the currently preferred embodiment of the depth-mode display 102 employs color intensity mapping as a function of signal intensity, and further colored red or blue according to flow directions towards or away from the probe, those skilled in the art will appreciate that color intensity as a function of detected velocity may be employed instead. In such case, and as shown in FIG. 3, color intensity varies from the clutter cutoff magnitude to a maximum velocity magnitude, corresponding with one-half the pulse repetition frequency (PRF). Detected signals having a power below the noise threshold or above the selected upper power limit are ignored. FIG. 4 is a color figure that shows the Aiming mode display 100 in which the color intensity of the regions 104 and 106 vary as a function of detected velocity. Both the depth-mode display 102 and the spectrogram 108 are displayed relative to the same time axis, and the depth-mode display shows variation both in spatial extent and in color intensity with the same periodicity as the heart beat. Those skilled in the art will also appreciate that instead of varying color intensity solely as a function of signal amplitude or solely as a function of velocity, one could advantageously vary color intensity as a function of both signal amplitude and velocity.

The particularly depicted depth-mode display 102 shown in FIG. 1 shows a simplified display of a single, well-defined red region 104 and a single, well-defined blue region 106. Those skilled in the art will appreciate that the number and characteristics of colored regions will vary depending on ultrasound probe placement and orientation. Indeed, a catalogue of characteristic depth-mode displays can be provided to assist the user in determining whether a particularly desired blood vessel has, in fact, been located. Once the user finds the characteristic depth-mode display for the desired blood vessel, the user can then conveniently determine the depth at which to measure the spectrogram 108.

The Aiming mode 100 enables the user to quickly position the ultrasound probe, such as adjacent to an ultrasound window through the skull so that intracranial blood flow can be detected. Use of colorized representation of signal amplitude is particularly advantageous for this purpose, since a strong signal is indicative of good probe location and orientation. The use of colorized representation of flow velocity may not be as advantageous, except where blood flow velocities vary significantly over blood vessel cross-section. However, when attempting to monitor blood flow near appreciably moving tissue (e.g., cardiac motion above clutter cutoff velocity), colorized representation of flow velocities may be preferred.

Figure 5:
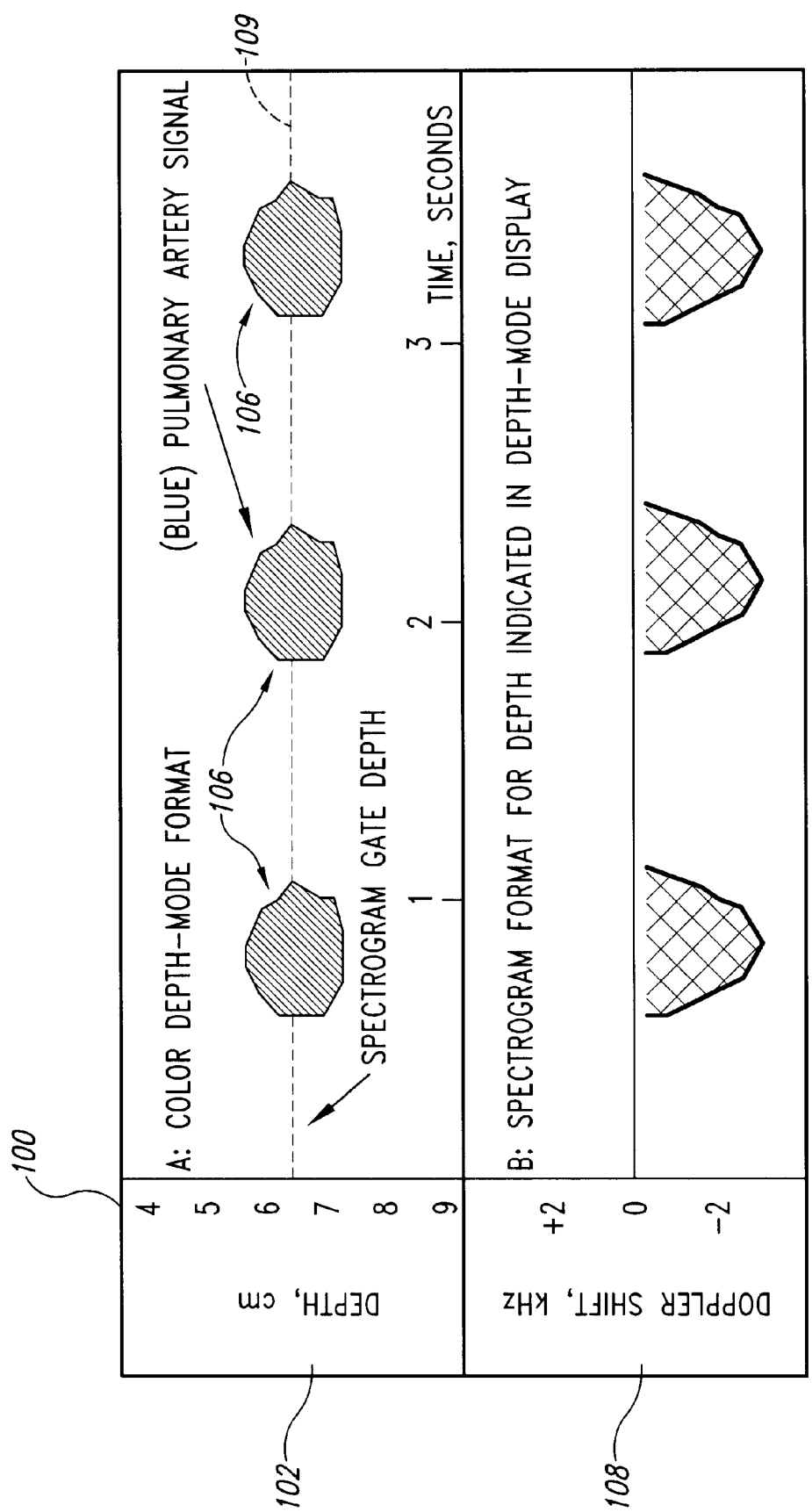
FIG. 5 is a graphical diagram depicting the display mode of FIG. 4 and its use to identify the pulmonary artery.

Referring to FIG. 5, use of the Aiming mode 100 is shown in connection with identifying a particular blood vessel, such as the pulmonary artery or femoral vein. In this case, a colorized representation of flow velocity is advantageously used in the depth-mode display 102, because of the high variation in blood flow velocities in these particular blood vessels. By observing the temporal variation in the depth-mode display 102, and the corresponding spectrogram 108, a user can identify optimal location of the pulmonary artery as follows: (1) the depth-mode display of the pulmonary artery will be blue with the same periodicity as the heart beat; (2) the blue region will typically reside between 4 and 9 cm depth; (3) along the time axis, the blue signal will be relatively intense in the middle of systole, corresponding to peak velocity; and (4) the signal will have the largest vertical extent in the depth-mode display, indicating that the user has positioned the probe such that the longest section of the pulmonary artery is aligned coincident with the ultrasound beam during systole. The user can then adjust other parameters, such as gate depth for the displayed spectrogram 108 and clutter filter parameters.

The Aiming mode 100 also indicates to the user where to set the depth of the pulse Doppler sample gate so that the spectrogram 108 will process Doppler shifts from desired blood flow signals. It is the spectrogram 108 that is of primary clinical interest, allowing the user to observe and measure parameters associated with a particular blood flow and providing information that might suggest hemodynamically significant deviations in that blood flow. Along with the depth-mode display 102 and the correspondingly selected spectrogram 108, the information displayed to a user also typically includes well-known numerical parameters associated with the spectrogram, such as mean peak systolic velocity, mean end diastolic velocity, pulsatility index, and the relative change in mean peak systolic velocity over time. Those skilled in the art will appreciate that other parameters and displays may also be provided, including data provided by other monitoring devices, such as EKG- or EEG-related information.

Figure 6:
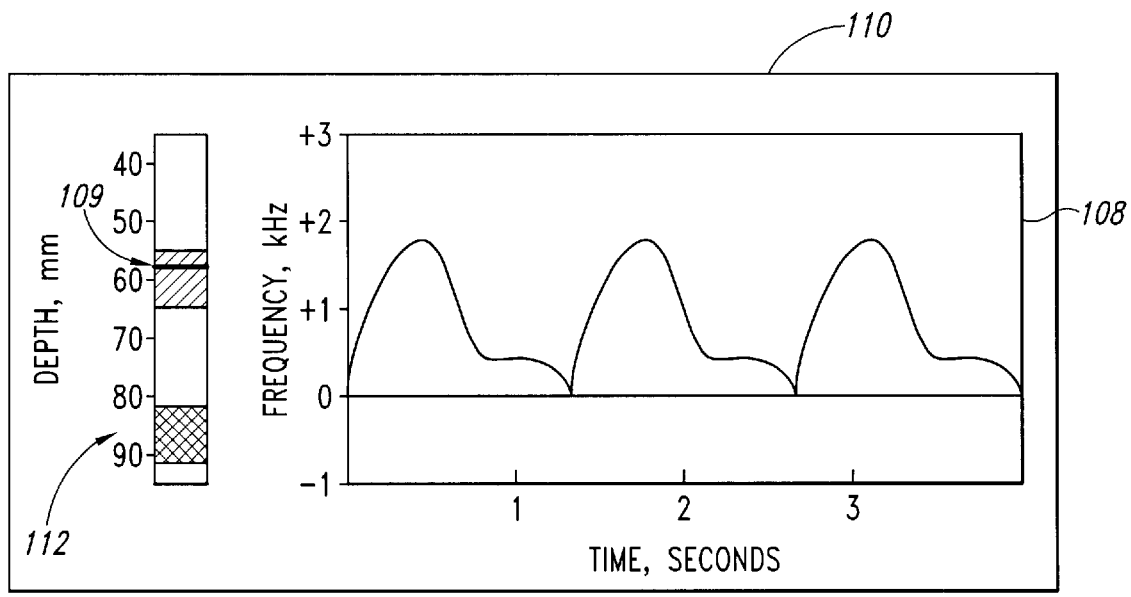
FIG. 6 is a graphical diagram depicting a second Doppler ultrasound system display mode in accordance with an embodiment of the invention.

The Aiming mode display 100 of FIG. 1 is particularly useful in positioning and orienting the Doppler ultrasound probe, and in first selecting a depth at which to measure the spectrogram 108. Following probe location and orientation and range gate selection, the user will typically prefer to have an information display emphasizing the clinically valuable spectrogram 108. Referring to FIG. 6, a second display mode is shown that is referred to as a Spectral mode 110. In this mode, the spectrogram 108 occupies a larger display area. Instead of the full depth-mode display 102, a compressed depth-mode display 112 is provided. This compressed depth-mode display 112, on a shortened time scale, provides information concerning the depth of the sample volume at which the spectrogram 108 is taken, and the status of the blood flow in that sample volume, towards or away from the probe Thus, the user is continually informed concerning the desired sample volume depth and associated blood flow. This allows for quick understanding and compensation for any changes in the location of the desired sample volume relative to the blood flow, such as due to probe motion. This also allows a user of the ultrasound system to fine tune the sample volume depth even while focusing primary attention on the clinically important spectrogram 108.

Figure 7:
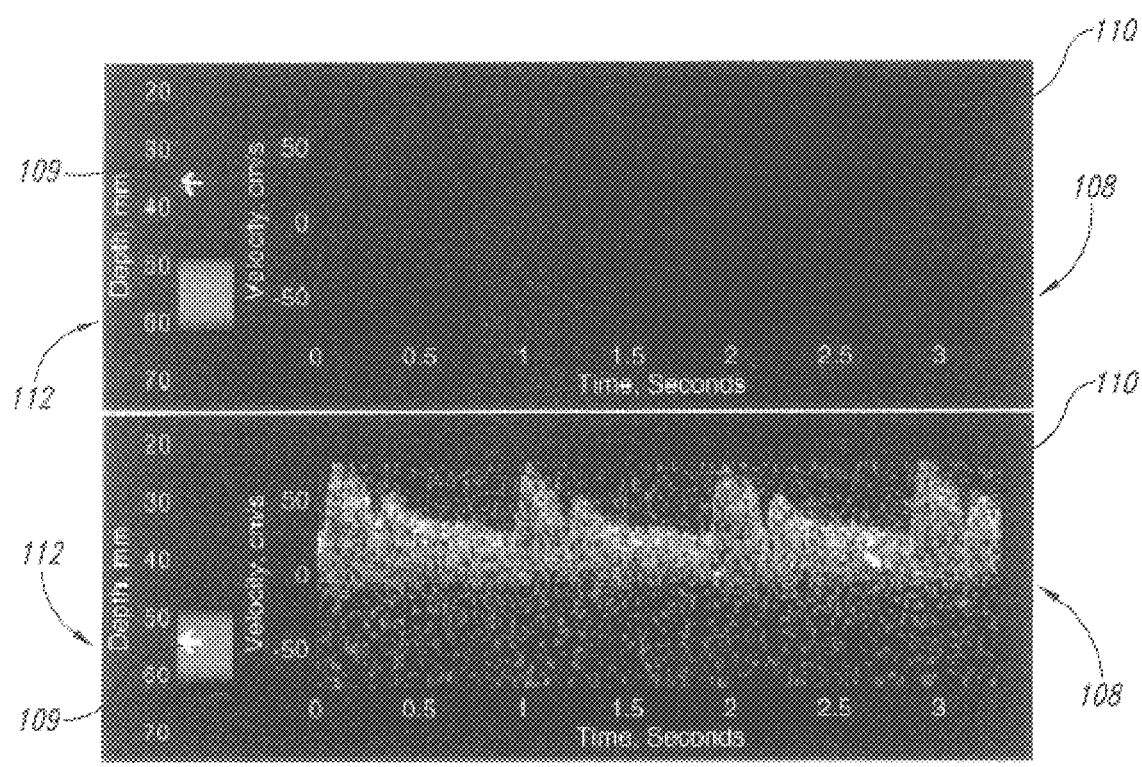
FIG. 7 shows two views of the display mode of FIG. 6 in color.

FIG. 7 shows two different views of the Spectral mode 110 in color. In one view, the selected depth indicated by the pointer 109 in the compressed depth-mode display 112 is not a location at which blood flows, and consequently no there are no blood flow signals in the displayed spectrogram 108. In the other view, the selected depth indicated by the pointer 109 does coincide with blood flow, and a corresponding spectrogram 108 is displayed. In the particular embodiment shown in FIG. 7, the color intensity of the region 104 varies as a function of detected velocity, and shows a characteristic color variation that may be associated with variation in blood velocity across blood vessel cross-section, a variation with depth in the alignment of the detected blood flow relative to the ultrasound beam axis, or both.

Those skilled in the art will appreciate the important advantages provided by the diagnostic information displays shown in FIGS. 1, 4, 6, and 7. While the displayed spectrogram 108 is not itself new, today's pulse Doppler ultrasound systems that do not have B-mode capability lack a means for successfully and reliably locating and orienting an ultrasound probe and determining an appropriate sample volume depth at which to detect the blood flow of interest. Also, while colorized representation of blood flow directions and speeds or signal amplitude is well known in the art, such as in color M-mode displays, such displays have not been used for the purpose of aiming ultrasound probes or in selecting particular sample volume depths for concurrent spectrogram analysis.

Figure 8:
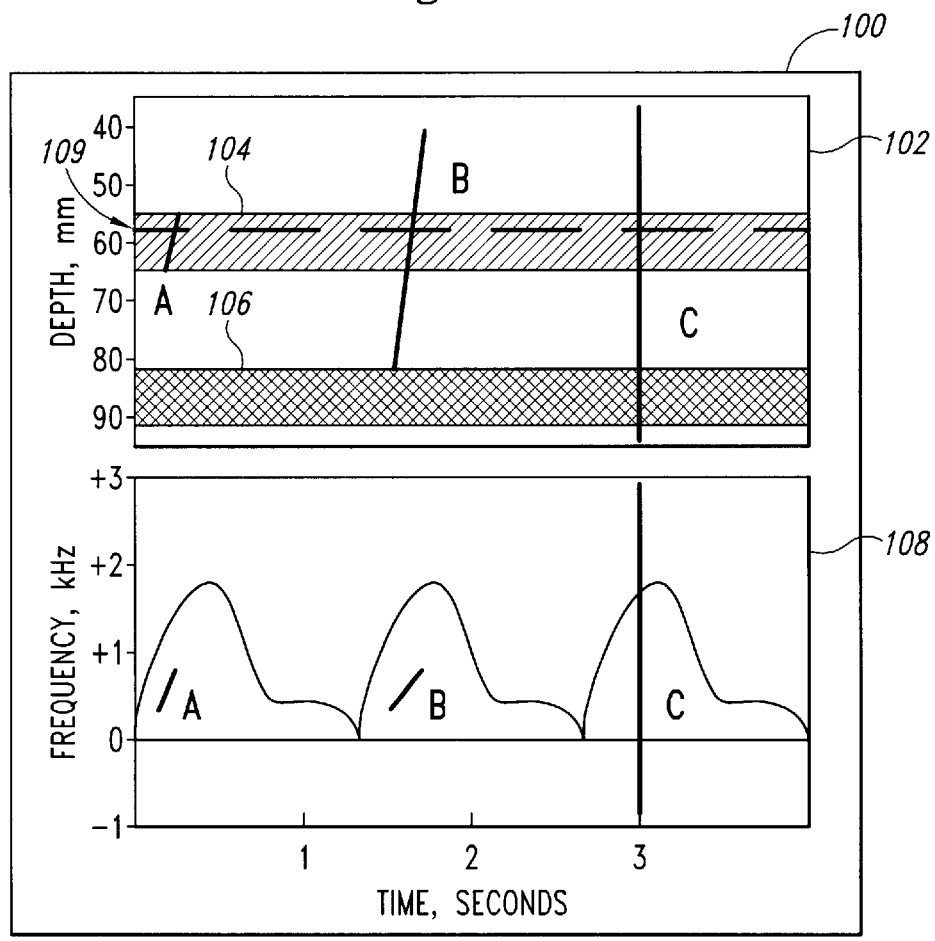
FIG. 8 is the graphical diagram of the display mode shown in FIG. 1, further depicting and distinguishing embolic signals from artifact signals.

Referring to FIG. 8, the simultaneous presentation of the depthmode display 102 and spectrogram 108 can also provide important information for detecting embolic signals and differentiating such signals from non-embolic artifacts. FIG. 8 depicts three events: A, B, and C. In event A, the depth-mode display 102 shows a particularly high intensity signal having a non-vertical slope—i.e., a high-intensity signal that occurs at different depths at different times. In event A, the signal exists only within the boundary of one of the colored blood flow regions 104 and 106. In the spectrogram 108, a particularly high intensity signal is seen to have different velocities, bounded by the maximum flow velocity, within a short temporal region within the heartbeat cycle. Event A is strong evidence of an embolus passing through a blood flow region near the selected sample volume.

Event B is another likely candidate for an embolus. In this case, the high-intensity signal seen in the depth-mode display 102 is non-vertical, but does not appear exclusively within a range of depths where blood is flowing. While this signal is strong enough and/or has a long enough back scatter to appear outside the blood flow margin in the depth-mode display 102, the spectrogram display 108 still shows the characteristic high intensity transient signal associated with an embolus. Event B is also evidence of an embolus, but likely an embolus different in nature from that associated with event A. Although the particular signal characteristics of various emboli have not yet been fully explored in the depth-mode display, the distinction between events A and B is likely that of different embolus types. For example, event A may be associated with a particulate embolus, whereas event B may be associated with a gaseous embolus, with the different acoustic properties of a gas bubble causing the particularly long back scatter signal and the appearance of occurrence outside the demonstrated blood flow margins.

Event C is an artifact, whether associated with probe motion or some other non-embolic event. Event C appears as a vertical line in the depth-mode display 102, meaning that a high-intensity signal was detected at all depth locations at precisely the same time—a characteristic associated with probe motion or other artifact. Similarly, the high-intensity signal displayed in the spectrogram display 108 is a vertical line indicating a high-intensity signal detected for a wide range of velocities (including both positive and negative velocities and velocities in excess of the maximum blood flow velocities) at precisely the same time. Event C then is readily characterized as an artifact signal, and not embolic in nature.

Those skilled in the art will appreciate that the simultaneous display of the depth-mode display 102 and the spectrogram 108 provides not only convenient means for locating the desired sample volume, but also provides a particularly useful technique for distinguishing embolic signals from artifact signals, and perhaps even for characterizing different embolic signals. Such embolic detection and characterization is easily observed by the operator, but can also be automatically performed and recorded by the ultrasound apparatus.

Automatic embolus detection is provided by observing activity in two or more sample gates within the blood flow at the same time. The system discriminates between two different detection hypotheses:

(1) If the signal is embolic, then it will present itself in multiple sample gates over a succession of different times.

(2) If the signal is a probe motion artifact, then it will present itself in multiple sample gates simultaneously.

These two hypotheses are mutually exclusive, and events that are declared embolic are done so after passing the "Basic Identification Criteria of Doppler Microembolic Signals" (see, for example, *Stroke,* vol. 26, p. 1123, 1995) and verifying that successive detection (by time-series analysis or other suitable technique) of the embolic signal in different sample gates is done at different points in time, and that the time delay is consistent with the direction of blood flow. The differentiation of embolic from artifact signals can be further confirmed by also observing activity at one or more sample gates outside the blood flow.

Figure 9:
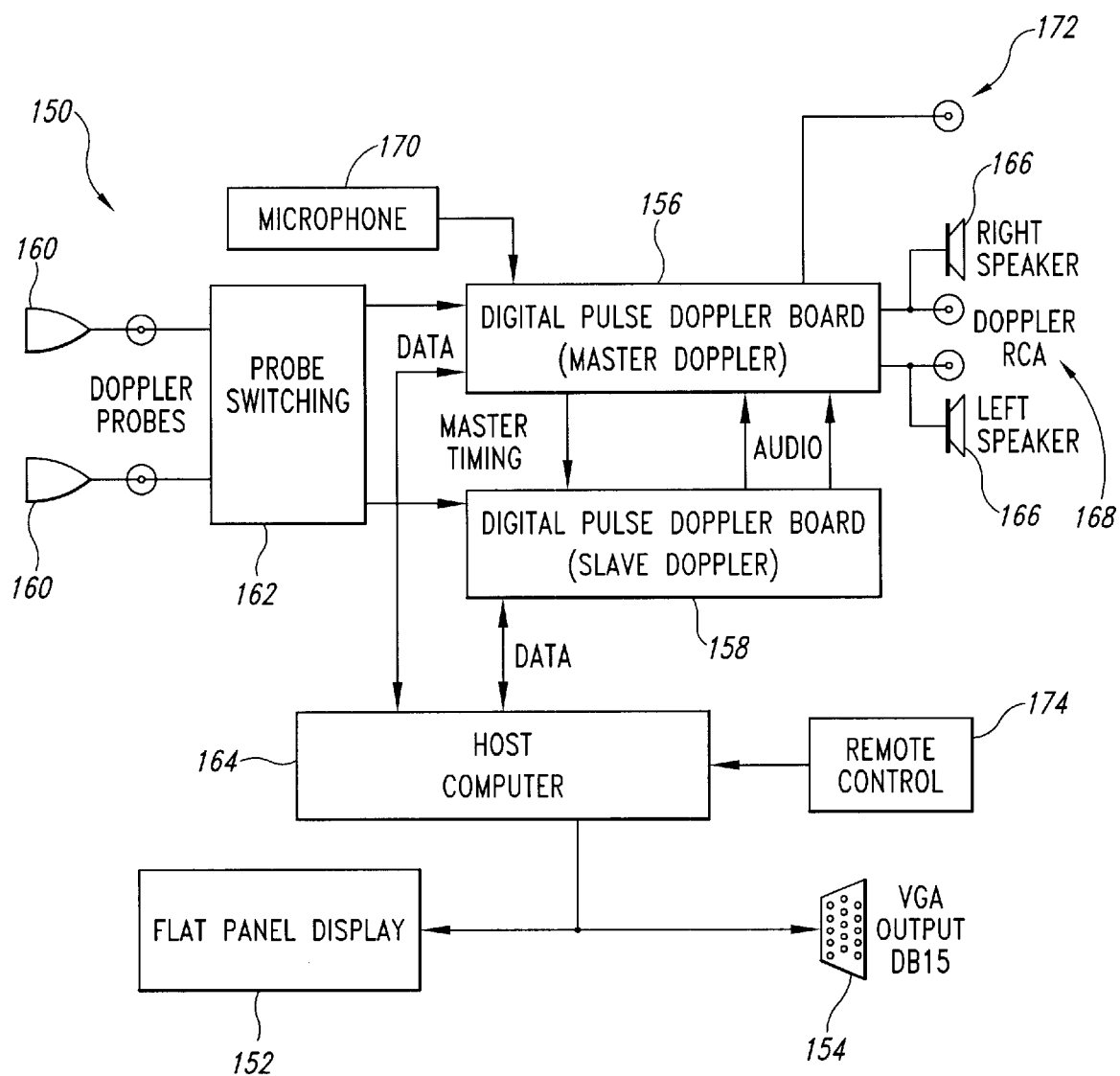
FIG. 9 is a functional block diagram depicting a Doppler ultrasound system in accordance with an embodiment of the invention.

FIG. 9 is a functional block diagram that depicts an ultrasound system 150 in accordance with an embodiment of the invention. The ultrasound system 150 produces the various display modes described above in connection with FIGS. 1–8 on an integrated flat panel display 152 or other desired display format via a display interface connector 154. The signal processing core of the Doppler ultrasound system 150 is a master pulse Doppler circuit 156 and a slave pulse Doppler circuit 158. The Doppler probes 160 are coupled with other system components by a probe switching circuit 162. The probe switching circuit 162 provides both presence-detect functionality and the ability to distinguish between various probes, such as by detecting encoding resistors used in probe cables or by other conventional probe-type detection. By providing both the master and slave pulse Doppler circuits 156 and 158, two separate ultrasound probes 160 may be employed, thereby providing unilateral or bilateral ultrasound sensing capability (such as bilateral transcranial measurement of blood velocity in the basal arteries of the brain). The master and slave pulse Doppler circuits 156 and 158 receive the ultrasound signals detected by the respective probes 160 and perform signal and data processing operations, as will be described in detail below. Data is then transmitted to a general purpose host computer 164 that provides data storage and display. A suitable host computer 164 is a 200 MHz Pentium processor-based system having display, keyboard, internal hard disk, and external storage controllers, although any of a variety of suitably adapted computer systems may be employed.

The ultrasound system 150 also provides Doppler audio output signals via audio speakers 166, as well as via audio lines 168 for storage or for output via an alternative medium. The ultrasound system 150 also includes a microphone 170 for receipt of audible information input by the user. This information can then be output for external storage or playback via a voice line 172. The user interfaces with the ultrasound system 150 primarily via a keyboard or other remote input control unit 174 coupled with the host computer 164.

Figure 10:
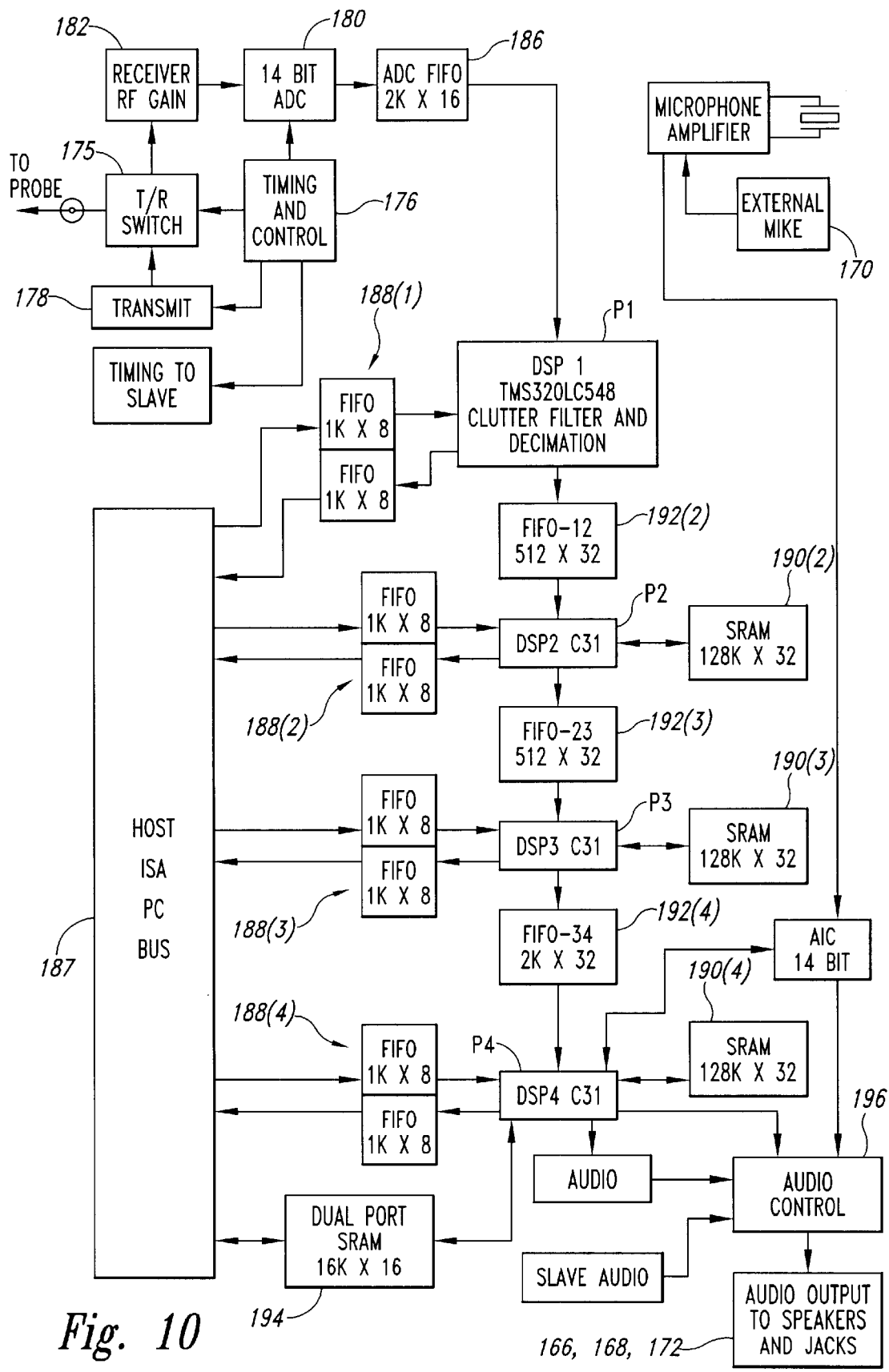
FIGS. 10 and 11 are functional block diagrams depicting particular details of pulse Doppler signal processing circuitry included in the Doppler ultrasound system of FIG. 9.
Figure 11:
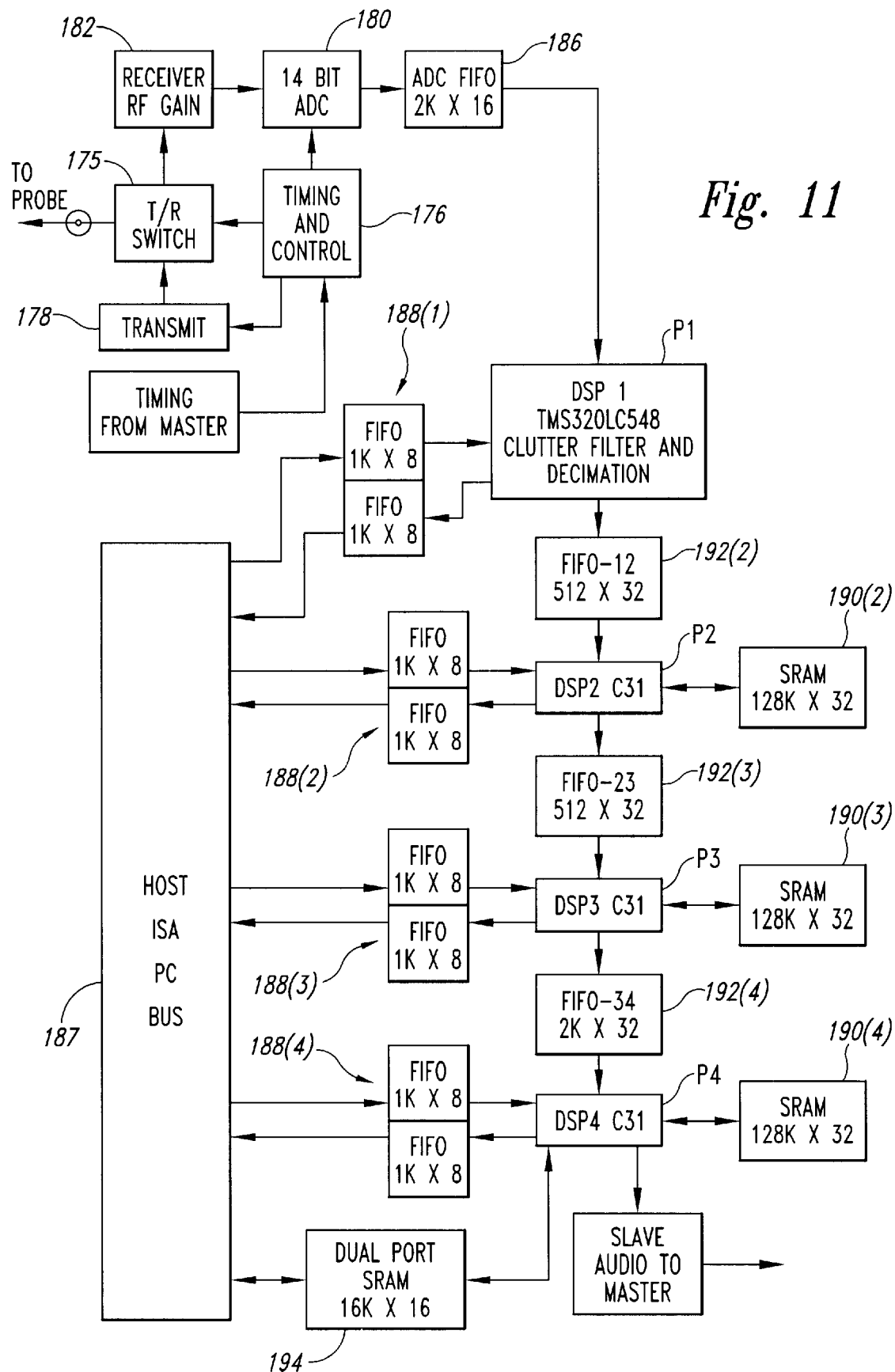

FIGS. 10 and 11 depict particular details of the master and slave pulse Doppler circuits 156 and 158. To the extent FIGS. 10 and 11 depict similar circuit structures and interconnections, these will be described once with identical reference numbers used in both Figures. FIG. 10 also depicts details concerning the input and output of audio information to and from the ultrasound system 150 via the microphone 170, the speakers 166, and the audio output lines 168 & 172, the operations of which are controlled by the master pulse Doppler circuit 156.

At the transducer input/output stage, each of the pulse Doppler circuits 156 and 158 includes a transmit/receive switch circuit 175 operating under control of a timing and control circuit 176 (with the particular timing of operations being controlled by the timing and control circuit 176 of the master pulse Doppler circuit 156). The timing and control circuit 176 also controls operation of a transmit circuit 178 that provides the output drive signal causing the Doppler probes 160 (see FIG. 9) to emit ultrasound. The timing and control circuit 176 also controls an analog-to-digital converter circuit 180 coupled to the transmit/receive switch 175 by a receiver circuit 182. The function and operation of circuits 175–182 are well known to those skilled in the art and need not be described further.

The primary signal processing functions of the pulse Doppler circuits 156 and 158 are performed by four digital signal processors P1–P4. P1 is at the front end and receives digitized transducer data from the receiver 182 via the analog-to-digital converter circuit 180 and a data buffer circuit or FIFO 186. P4 is at the back end and performs higher level tasks such as final display preparation. A suitable digital signal processor for P1 is a Texas Instruments TMS320LC549 integer processor, and suitable digital signal processors for P2–P4 are Texas Instruments TMS320C31 floating point processors, although other digital signal processing circuits may be employed to perform substantially the same functions in accordance with the invention.

Received ultrasound signals are first processed by the digital signal processor P1 and then passed through the signal processing pipeline of the digital signal processors P2, P3, and P4. As described in detail below, the digital signal processor P1 constructs quadrature vectors from the received digital data, performs filtering operations, and outputs Doppler shift signals associated with 33 different range gate positions. The digital signal processor P2 performs clutter cancellation at all gate depths. The digital signal processor P3 performs a variety of calculations, including autocorrelation, phase, and power calculations. P3 also provides preparation of the quadrature data for stereo audio output. The digital signal processor P4 performs most of the calculations associated with the spectrogram display, including computation of the spectrogram envelope, systole detection, and also prepares final calculations associated with preparation of the Aiming display.

Each of the digital signal processors P1–P4 is coupled with the host computer 164 (see FIG. 9) via a host bus 187 and control data buffer circuitry, such as corresponding FIFOs 188(1)–188(4). This buffer circuitry allows initialization and program loading of the digital signal processors P1–P4, as well as other operational communications between the digital signal processors P1–P4 and the host computer. Each of the digital signal processors P2–P4 is coupled with an associated high-speed memory or SRAM 190(2)–190(4), which function as program and data memories for the associated signal processors. In the particularly depicted signal processing chain of FIG. 10 or 11, the digital signal processor P1 has sufficient internal memory, and no external program and data memory need be provided. Transmission of data from one digital signal processor to the next is provided by intervening data buffer or FIFO circuitry 192(2)–192(4). The ultrasound data processed by the digital signal processor P4 is provided to the host computer 164 via data buffer circuitry such as a dual port SRAM 194.

Referring to FIG. 10, the digital signal processor P4 of the master pulse Doppler circuit 156 also processes audio input via the microphone 170, as well as controlling provision of the audio output signals to the speakers 166 and audio output lines 168, 172. P4 controls the audio output signals by controlling operations of an audio control circuit 196, which receives audio signals from both the master and the slave pulse Doppler circuits 156 and 158.

Referring to process flow charts shown in FIGS. 12–16, a detailed description will now be provided of the operations performed by of each of the digital signal processors P1–P4 included in both the master and slave pulse Doppler circuits 156 and 158. Particular detailed calculations and numerical information are provided to disclose a current embodiment of the invention, but those skilled in the art will appreciate that these details are exemplary and need not be included in other embodiments of the invention.

Figures 12, 13:
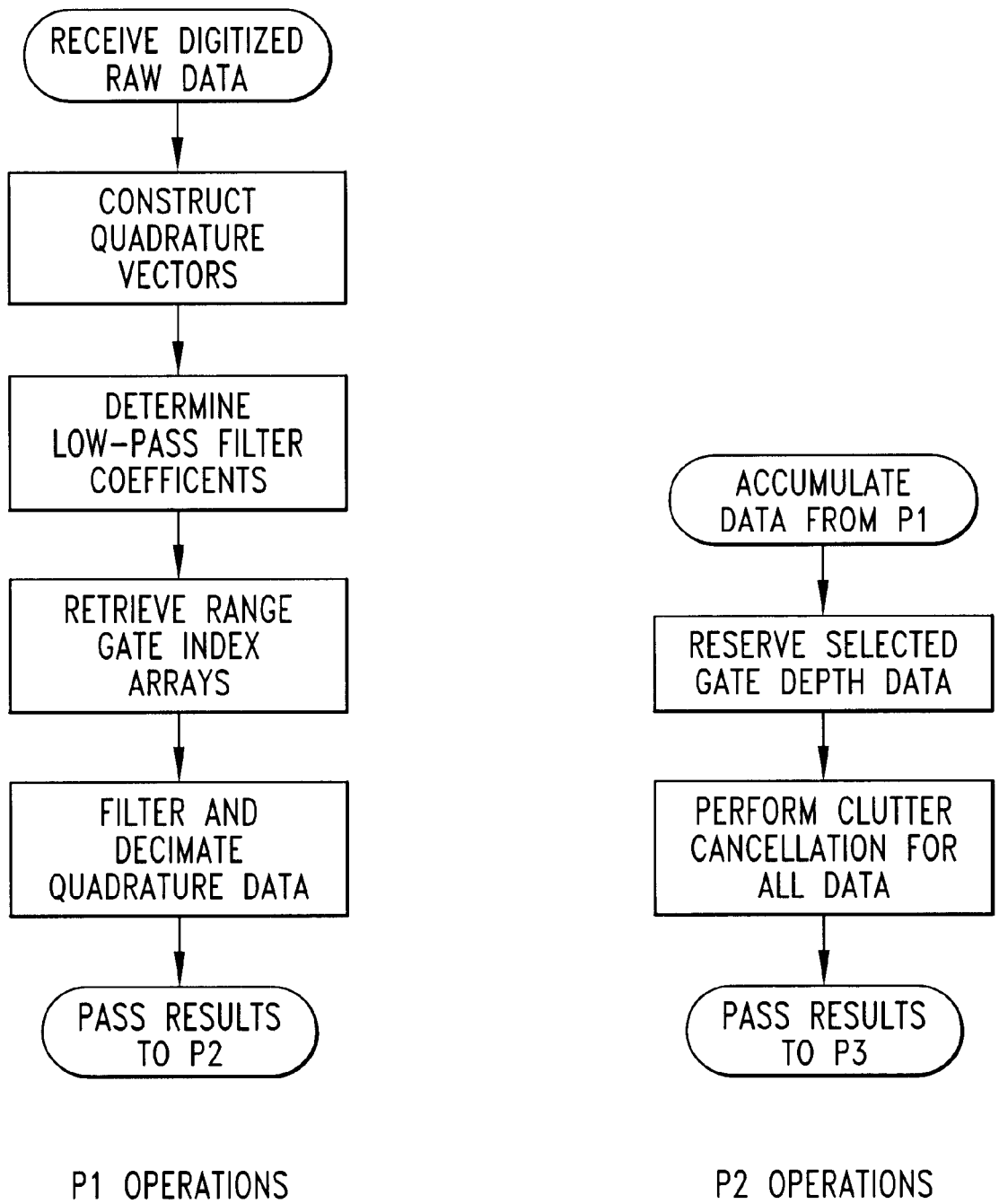
FIGS. 12–18 are process flow charts depicting particular operations performed by the pulse Doppler signal processing circuitry of FIGS. 10 and 11.

Referring to FIG. 12, the operations of digital signal processor P1 are as follows:

1. DIGITIZATION OF RAW DATA. Read A(1:N), a series of N 14-bit values from the input A/D. The values are converted at 4× the Doppler carrier frequency (8 MHz), and commence synchronously with the start of the transmit burst. N=1000 if the Doppler pulse repetition frequency (PRF) is 8 kHz, 1280 if the Doppler PRF is 6.25 kHz, and 1600 if the Doppler PRF is 5 kHz.

2. QUADRATURE VECTOR CONSTRUCTION. Construct two vectors with N/4 points each according to the following rules: $Br(1:N/4)=A(1:4:N-3)-A(3:4:N-1)$, and $Bi(1:N/4)=A(2:4:N-2)-A(4:4:N)$. Br and Bi are the digitally demodulated quadrature Doppler values for a series of N/4 different gate depths. The subtractions here remove DC bias from the data.

3. LOW-PASS FILTER COEFFICIENTS. Br and Bi contain frequencies within a bandwidth equal to the carrier frequency and centered on DC, and need to be further filtered to remove noise outside the bandwidth of the Doppler transmit burst. The coefficients for accomplishing this low-pass filtering are determined by a creating, with standard digital filter design software such as MATLAB, an order 35 low-pass FIR filter. The normalized cutoff of this filter is $2/(T*fs)$, where T is the time duration of the transmit burst, and fs is the sample rate of the data in Br and Bi (2 MHz). Call this filter $C(1:35)$. The coefficients of this filter will vary as the transmit burst length is changed by the user, and a bank of several different sets of filter coefficients is accordingly stored to memory.

4. INDEX ARRAYS. Data from 33 range gate positions are to be processed and passed onto P2. For ease of graphical display, these range gate positions are selected to be 2 mm apart. However, the quadrature vectors Br and Bi do not contain elements that are spaced 2 mm apart-they are 0.385 mm apart. Therefore, indices into the Br and Bi arrays are used that correspond to values falling closest to multiples of 2 mm, as a means to decimating Br and Bi to 1 mm sampling increments. This is done by having a prestored array of indices, $D1(1:33)$, corresponding to depths 22:86 mm for 8 kHz PRF, and indices $D2(1:33)$ and $D3(1:33)$ with corresponding or deeper depth ranges for 6.25 kHz and 5 kHz PRFs.

5. LOW-PASS FILTER AND DECIMATION OF QUADRATURE DATA. The Br and Bi arrays are low-pass filtered and decimated to 33 gates by the following rules (note $<a,b>$ is the 32 bit accumulated integer dot product of vectors a and b):

8 kHz PRF:

$Er(j)=<C, Br(D1(j)+(-10:10))>$ $Ei(j)=<C, Bi(D1(j)+(-10:10))>$, and $j=1:33$.

6.25 kHz PRF:

$Er(j)=<C, Br(D2(j)+(-10:10))>$ $Ei(j)=<C, Bi(D2(j)+(-10:10))>$, and $j=1:33$.

5 kHz PRF:

$Er(j)=<C, Br(D3(j)+(-10:10))>$ $Ei(j)=<C, Bi(D3(j)+(-10:10))>$, and $j=1:33$.

6. PASS RESULTS TO P2. Er and Ei, 66 values altogether, comprise the Doppler shift data for 1 pulse repetition period, over a set of 64 different sample gates spaced approximately 2 mm apart. These arrays are passed to P2 with each new transmit burst.

Referring to FIG. 13, the operations of digital signal processor P2 are as follows:

1. ACCUMULATE INPUT DATA. Collect a buffer of M Er and Ei vectors from P1 over a period of 8 ms, into floating point matrices Fr and Fi. At the PRFs of [8,6.25,5]kHz, the matrices Fr and Fi will each contain respectively M=[64,50,40] vectors. The jth Er and Ei vectors at their respective destinations are denoted by Fr(1:33,j) and Fi(1:33,j) (these are column vectors). The kth gate depth across the M collected vectors is indexed by Fr(k,1:M) and Fi(k,1:M) (these are row vectors).

2. PRESERVATION OF RAW DATA AT "CHOSEN" GATE DEPTH. Reserve in separate buffer the raw data at the user-chosen gate depth, k, at which the Doppler spectrogram is processed. This row vector data, Gr(1:M)=Fr(k, 1:M) and Gi(1:M)=Fi(k,1:M), is passed forward to P3 and eventually to the host for recording purposes.

3. CLUTTER CANCELLATION. Apply a fourth order clutter cancellation filter to each row of Fr and Fi. Hr(1:33,1:M) and Hi(1:33,1:M) are the destination matrices of the filtered Fr(1:33,1:M) and Fi(1:33,1:M) data. Application of this filter with continuity requires maintaining state variables and some previous Fr and Fi values. The coefficients of the clutter filter will vary depending on the user choice of cutoff frequencies from 0 to 600 Hz in 25 Hz increments. These coefficients are available by table lookup in processor RAM, given the user choice from the above options.

4. PASS RESULTS TO P3. Gr, Gi, Hr and Hi are passed to P3 for further processing.

Figure 14:
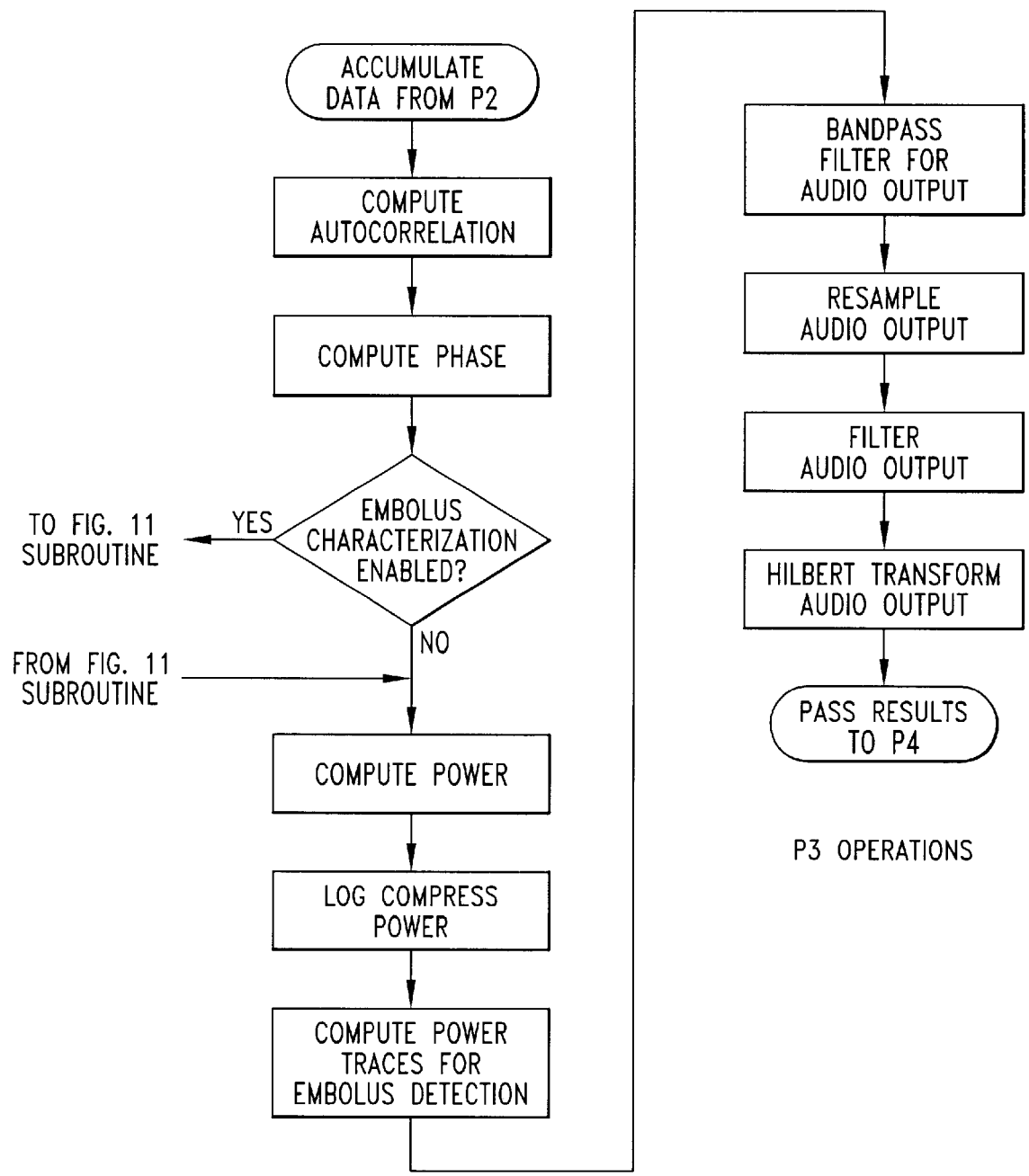

Referring to FIG. 14, the operations of digital signal processor P3 are as follows:

1. ACCUMULATE INPUT DATA. Receive Gr, Gi, Hr and Hi from P2.

2. COMPUTE AUTOCORRELATION. Compute the first lag of the autocorrelation of the data at each gate over time. Use all M values at each gate in this calculation. This will generate an array of 33 complex values, one for each gate. For the kth gate depth, let P=Hr(k,1:M)+jHi(k,1:M). Then the first lag autocorrelation for this depth is AC(k)=<P(1:M−1),P(2:M)>. (Note that in a dot product of complex values, the second vector is conjugated. Also note that this and all dot products in P2, P3, or P4 are floating point calculations.) In this manner, construct the complex vector AC(1:33).

3. COMPUTE PHASE FOR EACH AC VALUE. For each autocorrelation value, us a four quadrant arctangent lookup to determine the phase of the complex value. Specifically, ANGLE(k)=arc tan(imag(AC(k)), real(AC(k))). The ANGLE(k) value is proportional to the mean flow velocity at the gate depth k.

4. If embolus characterization (e.g., distinguishing a particle from a bubble) capability is enabled, the method routes to a subroutine described below in connection with FIG. 16.

5. COMPUTE POWER. Compute the signal power. Use all M values at each gate in this calculation. This will generate an array of 33 real values, one for each gate. For the kth gate depth, again let P=Hr(k,1:M)+jHi(k,1:M). Then the power for this depth is POWER(k)=<P(1:M),P(1:M)> (note that in a dot product of complex values, the second vector is conjugated). In this manner, construct the real vector POWER(1:33).

6. LOG COMPRESS POWER. Convert POWER to Decibels: POWERd(1:33)=10*log 10(POWER(1:33)).

7. COMPUTE POWER TRACES FOR EMBOLUS DETECTION. For each of four preset gate depths (one being the user selected depth and the other three being correspondingly calculated), compute power from a 60 point moving window at M different positions of the window. Note that some history of the data at the specific gate depths will be required to maintain this calculation without interruption from new data spilling in every 8 ms. Specifically, for gate n, POWER_TRACEn(i)=<Hr(n,i−59:i)+jHi(n,i−59:i), Hr(n,i−59:i)+jHi(n,i−59:i)>. Note 3 power traces are taken from the region including the sample volume placed inside blood flow, while the fourth power trace is taken from a sample volume well outside the blood flow.

8. COMPLEX BANDPASS FILTER FOR USE IN AUDIO OUTPUT PREPARATION. The min and max frequencies resulting from user specified spectral unwrapping of the spectrogram are used to determine a complex bandpass filter for making the audio output sound congruent with what is shown on the spectrogram display. For example, if the unwrapping occurs at [−1,7]kHz, then the audio complex bandpass filter has edges at −1 kHz and +7 kHz. A bank of several sets of complex bandpass filter coefficients, corresponding to different unwrap ranges, is generated offline and placed in memory. Each coefficient set corresponds to one of the unwrapping selections the user can make. Let the operative set of filter coefficients be called UWa(1:O) and UWb(1:O), where O is the filter order plus one.

9. AUDIO OUTPUT PREPARATION: RESAMPLE. At the gate depth selected by the user, k, the Doppler shift signals are to be played out the audio speakers. Before doing so, some prepping of the audio signals is important to match the user-selected spectral unwrapping. Resample the audio signal Hr(k,1:M) and Hi(k,1:M) to twice the PRF by multiplexing the respective arrays with zeros: Qr(k,1:2M)={Hr(k,1), 0, Hr(k,2), 0, Hr(k,3), 0, . . . , Hr(k,M), 0} and Qi(k,1:2M)={Hi(k,1), 0, Hi(k,2), 0, Hi(k,3), 0, . . . , Hi(k,M), 0}.

10. AUDIO OUTPUT PREPARATION: COMPLEX BANDPASS. Apply a complex bandpass filter to Qr+jQi in order to remove the extra images introduced by multiplexing the data with zeros:

$$R(n)=UWb(1)*Q(n)+UWb(2)*Q(n-1)+ \ldots +UWb(O)*Q(n-O+1)$$

$$-Uwa(2)*R(n-1)-Uwa(3)*R(n-2)- \ldots -Uwa(O)*R(n-O+1)$$

where $Q(k)=Qr(k)+jQi(k)$.

11. AUDIO OUTPUT PREPARATION: HILBERT TRANSFORM. The audio data in the sequence R(n) is in quadrature format and needs to be converted into stereo left and right for playing to the operator. This is done with a Hilbert transform, and a 95 point transform, H(1:95), is used in this work—the coefficients can be obtained with formulas in the literature or standard signal processing software such as MATLAB. The application of the Hilbert transform to a data sequence is done as an FIR filter. Construction of stereo separated signals RL and RR from R(n) is done according to [RL=Hilbert(Rr)+Delay(Ri), RR=Hilbert(Rr)−Delay(Ri)] where Delay is a (Nh+1)/2 step delay of the imaginary component of R, and Nh is the size of the Hilbert filter (95).

12. Pass Gr, Gi, ANGLE, POWERd, POWER_TRACE1, POWER_TRACE2, POWER_TRACE3, POWER_TRACE4, Rr, Ri, RL and RR to P4 for further processing.

Figure 15:
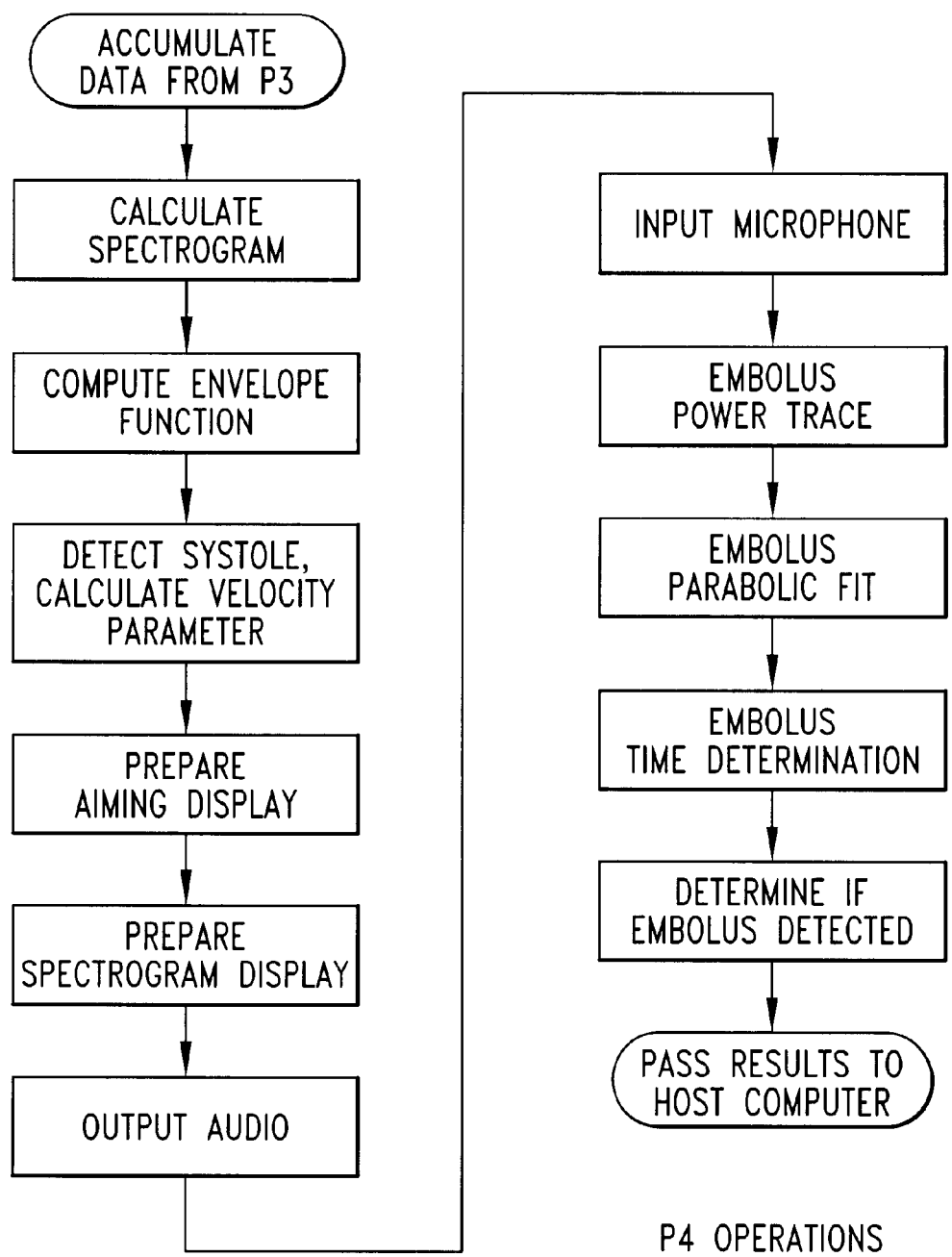

Referring to FIG. 15, the operations of digital signal processor P4 are as follows:

1. ACCUMULATE INPUT DATA. Receive Gr, Gi, ANGLE, POWERd, POWER_TRACE1, POWER_TRACE2, POWER_TRACE3, POWER_TRACE4, Rr, Ri, RL and RR from P3.

2. CALCULATE SPECTROGRAM. Compute power spectrum via the following steps: a) Concatenate new points in the Rr+jRi sequence with old points such that there are 128 points altogether, b) Multiply the 128 point sequence against a 128 point Hanning window, c) Calculate P, the FFT of the 128 point sequence, d) Calculate Pd=10*log 10(P), and e) FFTSHIFT the Pd sequence such that DC is at its center.
3. ENVELOPE. Compute the maximum frequency follower or "envelope" function, E(j), which indicates the upper edge of the flow signals in the spectrogram. This is an integer between 0 and 63, and is indexed by FFT calculation—i.e., for every spectral line calculation there is one value of E. Those skilled in the art will know of a variety of algorithms for making this calculation.
4. SYSTOLE DETECTION. Based on the maximum frequency follower, detect the start of systole. When the systolic start has been determined, set SYSTOLE_FLAG=TRUE. Also calculate the end diastolic velocity value, VEND, the peak systolic velocity value, VPEAK, and the mean velocity, VMEAN.
5. AIMING DISPLAY PREPARATION. Prepare the Aiming display via the following steps: a) Subtract the value of the "aim noise" parameter set by the user from the POWERd array: POWERd2=POWERd-aim_noise, b) multiply POWERd2 by a factor which is 64 (the number of color shades) divided by the value of the "aim range" parameter set by the user—POWERd3=POWERd2*64/aim_range, c) clip the resulting power data at 0 on the low end and 63 on the high end—the values now correspond to entries in a 64-value red or blue color table, and place results in array POWERd4, and d) multiply each of the power values by 1, 0 or −1, depending respectively on whether the associated ANGLE value is greater than the "filter cutoff parameter", less in absolute value than the filter cutoff parameter, or less than the negative of the filter cutoff parameter. This results in 64 values (one per gate depth) in the range of [−64,+63]. This modified aiming array, POWERd5, is ready to display after sending to the host computer.
6. SPECTROGRAM DISPLAY PREPARATION. Prepare the spectrogram display via the following steps: a) Subtract the user-selected noise floor parameter from the array Pd−Pd2=Pd-spectral_noise, b) Rescale the spectral data to contain 256 colors across the user-specified dynamic range—Pd3=Pd2*256/spectral_range, c) truncate/clip the data to be integer valued from 0 to 255—Pd4=min(255,floor(Pd3)), d) truncate the data to 8 bits—Pd5=8 bit truncate(Pd4).
7. AUDIO OUTPUT. Send the arrays RR and RL, the right and left speaker audio outputs, to the speakers via port writes.
8. INPUT MICROPHONE. Sample M values into vector MIC from the input microphone port (M is # of transmit pulse repetitions within an 8 ms period).
9. EMBOLUS DETECTION: BACKGROUND POWER IN POWER TRACES. For each of the four power traces, POWER_TRACE1 . . . POWER_TRACE4, corresponding to the four preset gate depths, compute a background power level. Recall that POWER_TRACEn contains M values, where M is # of transmit pulse repetitions within an 8 ms period). The background power value is obtained by a delta-follower for each trace, and is denoted by δ1, δ2, δ3, and d δ4.

δ1new=δ1old+Δ, where Δ=sign(δ1old-mean(POWER_TRACE1))*0.1 dB.

δ2new=δ2old+Δ, where Δ=sign(δ2old-mean(POWER_TRACE2))*0.1 dB.

δ3new=δ3old+Δ, where Δ=sign(δ3old-mean(POWER_TRACE3))*0.1 dB.

δ4new=δ4old+Δ, where Δ=sign(δ4old-mean(POWER_TRACE4))*0.1 dB.

This update in the background values is done once every M power values, or every 8 ms.
10. EMBOLUS DETECTION: PARABOLIC FIT. Apply a parabolic fit algorithm to the power trace each gate and determine if an event is occurring during the 8 ms period. This fit must be applied to successive data windows spaced apart by at most 1 ms. If the parabolic fit is concave down, and has a peak that exceeds the background power for the gate depth by 6 dB (an arbitrary threshold), then an event is detected.
11. EMBOLUS DETECTION: TIME DETERMINATION. For any single-gate events, compute the exact time of the event by analyzing the power trace between the −6 dB points on either side of the peak power of the event. Record event results and times so that current events may be compared to past ones.
12. EMBOLUS DETECTION: HIGH LEVEL CALCULATION. If the following conditions are true, then set DETECTION=TRUE: a) at least two adjacent of three gates in vicinity of blood flow show events within a 40 ms time window, b) the gate outside the blood flow shows no detection, and c) the timing of events shows progression in the direction of blood flow (i.e., the embolus is not swimming upstream).
13. Pass Gr, Gi, POWERdS, Pd5, SYSTOLE_FLAG, VEND, VMEAN, VPEAK, MIC and DETECTION to host for further processing.

Figure 16:
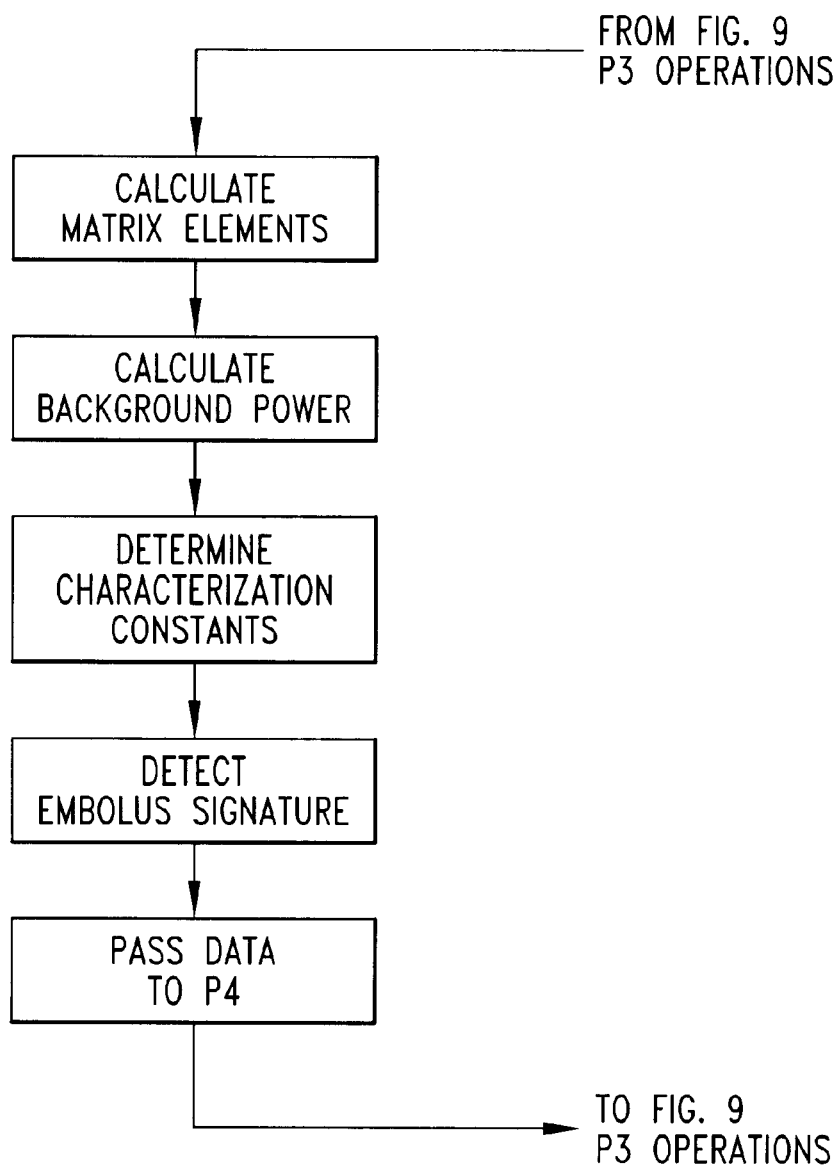

Referring to FIG. 16, the embolus characterization subroutine operations of digital signal processor P3 are as follows:
4A. CALCULATE MATRIX ELEMENT MAGNITUDES of Hr+jHi: Hmag(1:64,1:M)=10*log 10(Hr.^2+Hi.^2).
4B. CALCULATE REFERENCE BACKGROUND POWER LEVEL Pb. Hmean=sum(sum(Hmag(1:64,1:M)))/(64*M). IF PbOLD>Hmean THEN Pb=PbOLD−0.1 dB, ELSE Pb=PbOLD+0.1 dB. (This is a delta follower of the background power level).
4C. DETERMINATION OF R1 and R2, constants to be used in characterization. T1=transmit burst length in microseconds. T2=pulse repetition period, in microseconds. We know a priori that elements of Hk(1:64) are attached to 1 mm increments in depth. Then R1=axial resolution in mm=c*T1/2, where c=1.54 mm/microsecond, and R2=2*R1. For example, a 20 cycle transmit burst at 2 MHz carrier frequency has R1=7.2 mm, where R2=14.4 mm.
4D. DETECT EMBOLUS SIGNATURE by examining each column of Hmag(1:64,1:M) and determining longest contiguous segment of data such that each element in the contiguous segment is greater than Pb+XdB (X=3, e.g.). More specifically, let Hk(1:64)=Hmag(1:64,k). Locate longest sequence within Hk, demarcated by starting and ending indices Hk(i1:i2), such that Hk(i)>Pb+X if i1<=i<=i2. The length of this sequence is then determined by fitting the first three points of Hk(i1:i2) with a parabola, and finding the left most point on the abscissa, z1, where the parabola crosses the ordinate of Pb. If the parabola does not intersect the line y=Pb, then z1=i1. Similarly, the last three points of Hk(i1:i2) are fitted with a parabola and z2 is located. If the parabola does not intersect the line y=Pb, then z2=i2. The length of Hk(i1:i2) is z2−z1. IF z2−z1<R1, then no embolus is present. If R1<z2−z1<R2, then a particulate is present. If z2−z1>R2, then a bubble is present.

4E. Pass this information along to P4. If P4 agrees that an embolus is being detected, then attach the characterization information.

Figure 17:
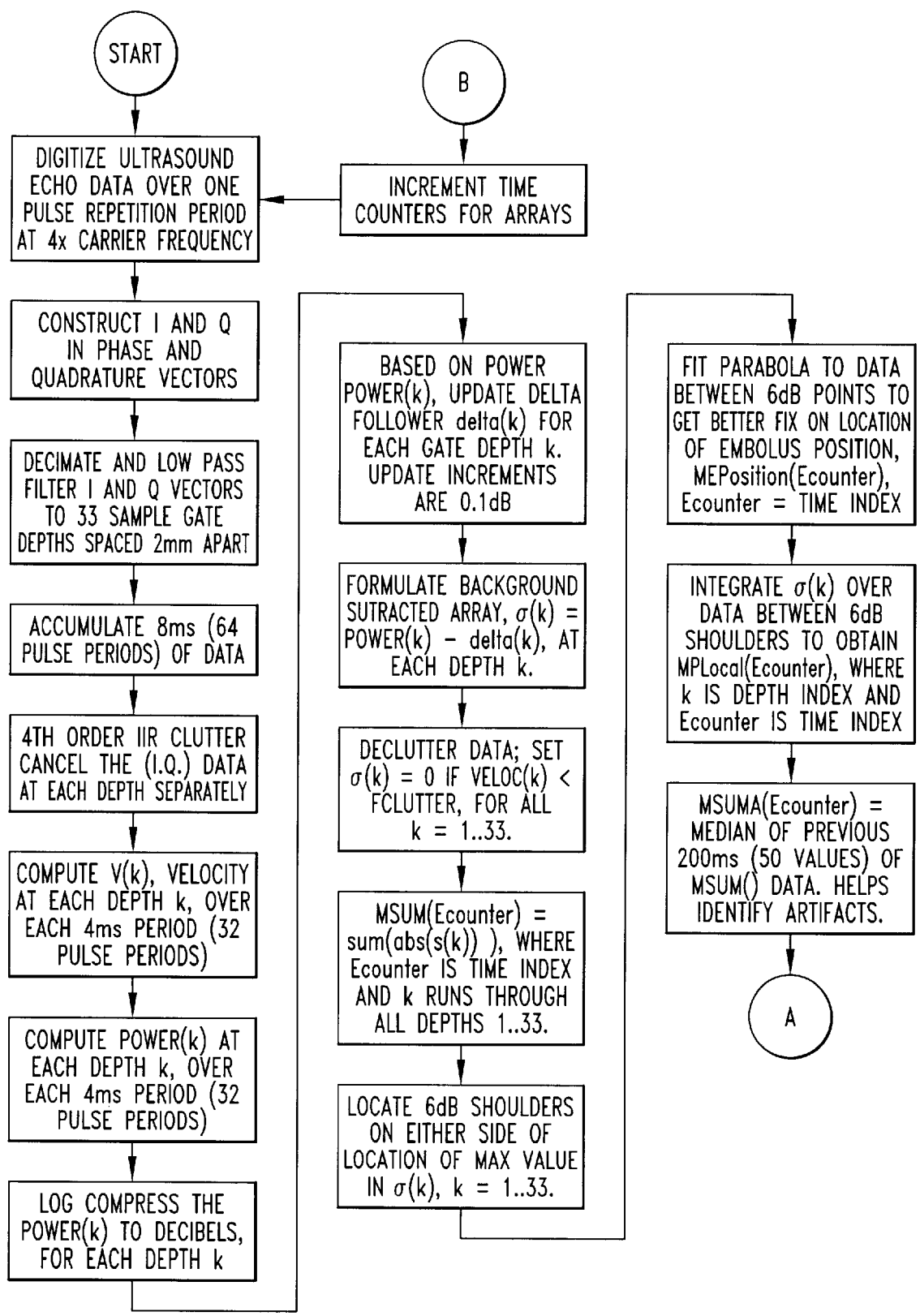
Figure 18:
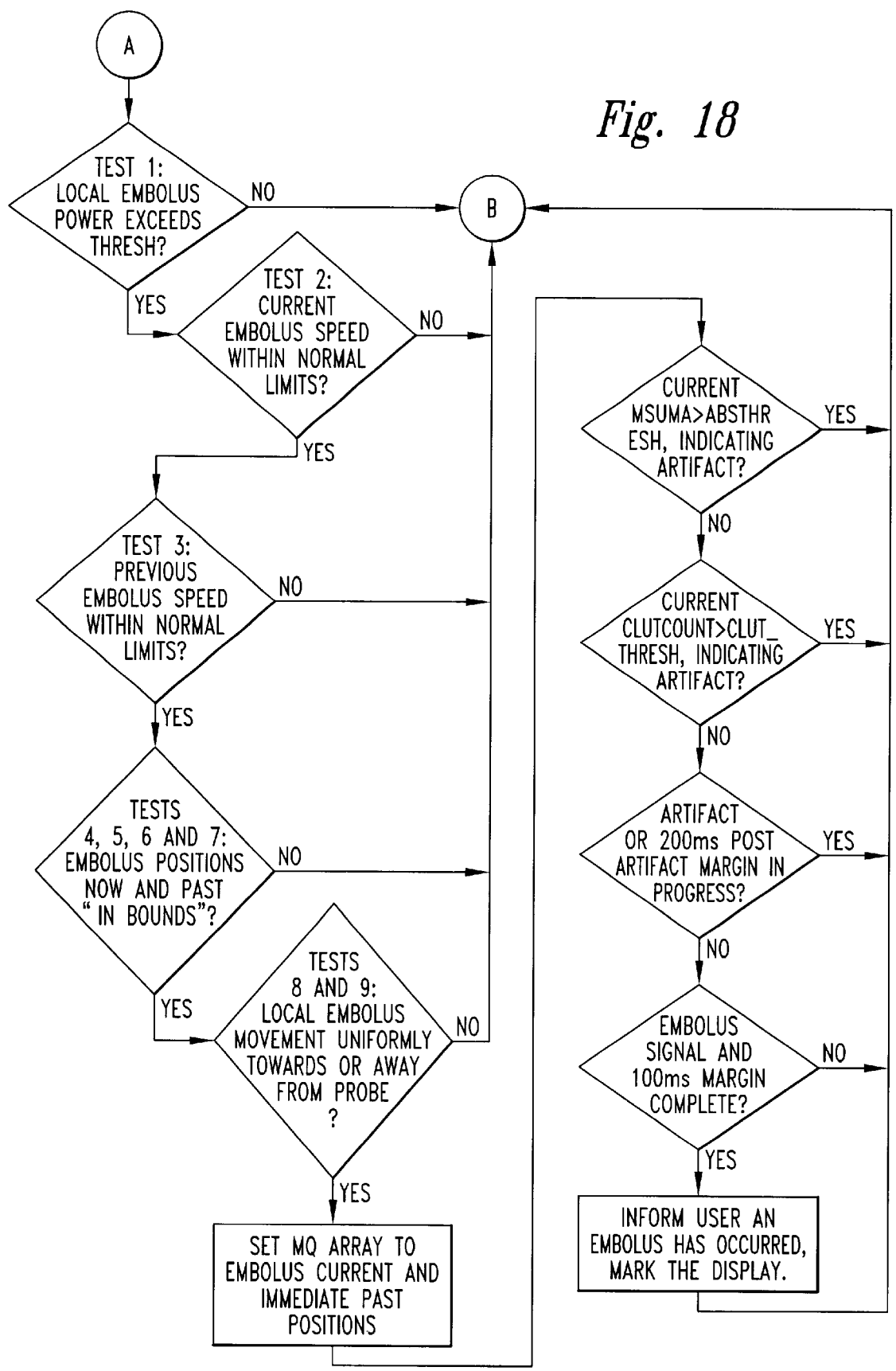

In addition to the method of embolus detection and characterization as previously discussed, the Doppler ultrasound system may be programmed to perform an alternative method of embolus detection as illustrated in FIGS. 17 and 18, and described below.

As previously discussed, embolus detection in conventional Doppler ultrasound devices typically relies on the Doppler signature sampled in one or two depth gates. Consequently, embolus detection capability is rather limited. However, in embodiments of the present invention, emboli can be tracked over a range of depths in the depth mode display 102 and may be counted and recorded based on their signature traversing a range of depths over time. As a result, the method for embolus detection of the present invention provides a user a more compelling argument for positively distinguishing an embolic signature from an artifact signal.

The embolus detection method illustrated in FIGS. 17 and 18 may be generally described in four algorithm parts. Although FIGS. 17 and 18 will be described below as including all four algorithm parts, as will be discussed in greater detail below, effective embolus detection may also be achieved by an embolus detection method having less than all four algorithm parts. Additionally, embolus detection may be made either automatically through software programming or Doppler ultrasound system design, or alternatively, by visual observation of the displayed information. The first part of the embolus detection algorithm removes non-transient signals that present relatively constant Doppler power at each gate depth. An example of these types of signals is cerebral blood flow signals that are detected in transcranial Doppler applications. The non-transient signals are removed through a process of keeping track of the background power at each depth comprising the m-mode image, and subtracting this background level so that only transient fluctuations in power remain. These remaining transient signals are typically representative of embolic events or unanticipated clutter or motion artifacts.

The second part removes low velocity clutter signals from the depth mode display 102. Examples of low velocity clutter artifact signals that may cause false positive identification in Doppler ultrasound systems having embolus detection based on single gate pulse Doppler are head taps ipsilateral and contralateral to the Doppler transducer, head taps on the front and back of the head, and jaw clenches. However, in embodiments of the present invention, motion artifact signals such as the ones previously described are removed by filtering signals having velocities less than a velocity threshold. Motion artifacts, unlike microemboli, tend to have broad band Doppler frequency signatures which span both positive and negative Doppler shift frequencies. This results in a zero or near-zero (below a velocity threshold) mean velocity. Thus, filtering signals having velocities less than a velocity threshold can effectively remove artifacts from the set of signals being tested for embolic properties. Consequently, motion artifacts for the most part revert to a black background color while embolic events appear with high contrast. Although the velocity threshold for removing signals may be set to various values, setting a velocity threshold of 7 cm/s (about 200 Hz Doppler shift) or less provides sufficient results for transcranial Doppler.

The third part of the embolus detection algorithm consists of reviewing a battery of questions aimed at determining from a priori physical understanding of microemboli whether a "candidate" event behaves in a manner consistent with an embolus. Examples of such tests include: (1) Does the embolus move in increments that do not exceed 8 mm each 4 ms (velocity of 2 m/s or less) (i.e., does the embolus stay close to higher known blood speeds and not jump off the map in this regard? and (2) In any group of three contiguous sightings of the embolus, does the embolus uniformly move either toward, or away from the transducer? If the entire battery of tests is affirmative, then the event is labeled embolic. It will be appreciated that many different questions may be included in the battery of tests. Consequently, the inclusion or omission of tests presently known or later developed should not limit the scope of the present invention.

The fourth algorithm part is conducted to flag embolic events with high specificity by performing additional operations to further rule out artifact signals. Some examples include excluding signals whose duration exceeds 200 ms, and ignoring candidate events detected in close proximity to a known artifact. Since emboli and artifacts tend to each be infrequent events, the chances of them occurring in close temporal proximity is deemed low. If these additional tests are passed, then the candidate event is labeled as an embolic event and is reported to the user.

The above four steps will now be described in greater detail. The first and second steps are illustrated in FIG. 17 and the third and fourth steps are illustrated in FIG. 18. It will be understood by one ordinarily skilled in the art that although this description utilizes the pulse repetition frequency of 8 kHz, other PRFs can be used as well. Prior to any embolus detection activity, Doppler power at all depths and Doppler shift frequency (i.e., velocity) at all depths are calculated as preparatory steps for embolus detection.

Although the zeroth and first lag autocorrelation technique is used in this embodiment for calculation of power and velocity, one skilled in the art will understand that other vehicles may be used, such as applying higher order autoregressive moving average (ARMA) parametric models to the data. Higher order ARMA models may be well suited to separating clutter, embolus and blood flow signals from each other. Certain flow conditions can arise in transcranial Doppler in which the m-mode display would be colored black under the above autocorrelation scenario. For example, certain places along the beam may correspond to sample volume positions for which the anterior cerebral artery and the internal carotid artery are seen simultaneously. Under this dual flow condition, the mean velocity will be near zero and the flow conditions would be presented as a dark background when filtered by the velocity threshold above. In this situation, a speckled blue and red background might be more informative to the user. An approach different from or in addition to autocorrelation which would address this situation is to apply a Hilbert transform to Doppler quadrature time series data at each gate depth, yielding stereo separated signals, one signal arising from scatterers moving away from the probe and the other signal arising from scatterers moving towards the probe. Analysis can then be done at each gate depth to determine: (1) if the stereo separated signals each have transient components, implying an artifact, (2) whether only one of the stereo separated signals has a transient component, implying an embolus, or (3) whether one or both of the stereo separated signals has true blood flow. Under the latter situation and in the absence of emboli or artifacts, a decision could be made whether to paint the m-mode display at the associated depth either blue or red or speckled or a third color, and with what intensity.

The power and velocity at all depths are used to generate the depth mode display, and may be calculated as described below. Although similar steps have been previously described with respect to FIGS. 12–15, several steps have been repeated below and illustrated in FIGS. 17 and 18 for the purposes of describing the alternative embolus detection method. The particular processors associated with each step are labeled P1 to P4, as above.

1. Preparation for Embolus Detection: Calculation of Power and Velocity over all Gate Depths Utilized in the Depth Mode Display a. DIGITIZATION OF RAW DATA (P1). The acoustic echo amplitude is loaded to digital memory for the entire period following the launch of an ultrasound pulse and prior to the next launch of an ultrasound pulse. The N values of data are sampled at 4 times the carrier frequency in order to enable fast demodulation to quadrature base band signals, as one skilled in the art will understand. Specifically, read A(1:N), a series of N 14-bit values from the input A/D. The values are converted at 4× the Doppler carrier frequency (8 MHz), and commence synchronously with the start of the transmit burst. N=1000, given the Doppler pulse repetition frequency (PRF) is 8 kHz.

b. QUADRATURE VECTOR CONSTRUCTION (P1). Inphase (I) and quadrature (Q) baseband samples of the Doppler shift signal are constructed from the acoustic echo sampled at 4 times the carrier frequency. This yields a series of (I, Q) pairs along the same time span as the acoustic echo sampling period, but sampled at the carrier frequency rate. The (I, Q) pairs are constructed by taking the difference between the first and third samples (to make I) and the second and fourth samples (to make Q) for each successive quartet of samples. Specifically, two vectors Br (in phase) and Bi (quadrature) are constructed with N/4 points according to the following rules: Br(1:N/4)=A(1:4:N−3)−A(3:4:N−1) and Bi(1:N/4)=A(2:4:N−2)−A(4:4:N). Br and Bi are the digitally demodulated quadrature Doppler values for a series of N/4 different gate depths.

c. LOW-PASS FILTER DESIGN. The baseband (I, Q) signal is decimated into the number of sampling depths used to make the depth mode display. Rather than sub-sampling the baseband (I, Q) signal and retaining noise over the full bandwidth equal to the carrier frequency, an FIR low pass filter (with bandwidth equal to that of the transmit burst) is employed to construct a new and smaller set of (I, Q) samples. The new set of (I, Q) samples is evenly distributed along a subrange of the Doppler pulse repetition period. Specifically, the coefficients for accomplishing this low-pass filtering are determined by creating, with standard digital filter design software such as MATLAB, an order 35 low-pass FIR filter. The normalized cutoff of this filter is 2/(T*fs), where T is the time duration of the transmit burst, and fs is the sample rate of the data in Br and Bi(2 MHz). Call this filter C(1:35). The coefficients of this filter will vary as the transmit burst length is changed by the user, and a bank of several different sets of filter coefficients is accordingly stored to memory.

d. INDEX ARRAYS. The decimation filtering discussed above is done at each desired gate depth to be used in constructing the depth mode power and velocity data. In this embodiment, data from 33 range gate positions are to be processed. For ease of graphical display, these range gate positions are selected to be 2 mm apart. Specifically, the input quadrature vectors to this processing stage, Br and Bi, do not contain elements that are spaced 2 mm apart—they are 0.385 mm apart. Therefore, application of the FIR decimation low-pass filter is done at positions in the Br and Bi arrays that correspond to values falling closest to multiples of 2 mm. This is done by having a pre-stored array of indices, D1(1:33), corresponding to depths 22:2:86 mm given 8 kHz PRF.

e. LOW-PASS FILTER AND DECIMATION OF QUADRATURE DATA (P1). The actual application of the decimation filter discussed above is done knowing the filter coefficients and the time positions along the pulse repetition period at which to apply the filter. Specifically, the Br and Bi arrays are low-pass filtered and decimated to 33 gates by the following rules (note <a, b> is the 36 bit accumulated integer dot product of vectors a and b):

$Er(j)=<C, Br(D1(j+(-17:17))>$ $Ei(j)=<C, Bi(D1(j+(-17:17))>$, and $j=1:33$.

Er and Ei, 66 values altogether, comprise the Doppler shift data for one pulse repetition period, over a set of 33 different sample gates spaced approximately 2 mm apart.

f. ACCUMULATE INPUT DATA (P2). The raw data (Doppler shift signal samples) along one pulse repetition period has been obtained. In this embodiment, 32 such pulse periods worth of data, spanning 4 ms, will be used to calculate one value of power and one value of velocity at each of the 33 gate depths. Specifically, a buffer of 32 Er and Ei vectors is collected over a period of 4 ms, into floating point matrices Fr and Fi. The jth Er and Ei column vectors are stored to Fr(1:33,j) and Fi(1:33,j). The kth gate depth across the M=32 collected vectors is indexed by Fr(k,1:M) and Fi(k,1:M) (row vectors). Note storage and subsequent calculations are floating point.

g. CLUTTER CANCELLATION (P2). The collected data is filtered, each depth separately, to remove clutter signals. Note that this does not entirely obliterate large clutter signals from still being present in the data, and this will be resolved in the embolus detection steps below. Specifically, a fourth order clutter cancellation filter is applied to each row of Fr and Fi. Hr(1:33,1:M) and Hi(1:33,1:M) are the destination matrices of the filtered Fr(1:33,1:M) and Fi(1:33,1:M) data. M=32 (i.e., 4 ms). Application of this filter with continuity in time requires maintaining state variables and some previous Fr and Fi values. The coefficients of the clutter filter will vary depending on the user choice of filter cutoff frequency, i.e., 25 Hz to 600 Hz in 25 Hz increments. These coefficients are available by table lookup in processor RAM, given the user choice from the above options.

h. COMPUTE VELOCITY AT EACH DEPTH (P3): STEP 1. Velocity is calculated in this embodiment by performing first lag autocorrelation at each gate depth. Specifically, compute the first lag of the autocorrelation of the data at each gate over the total time increment of 4 ms. For the kth gate depth, let P=Hr(k,1:M)+jHi(k,1:M). Then the first lag autocorrelation for this depth is AC(k)=<P(1:M−1), P(2:M)>. (Note that in a dot product of complex values, the second vector is conjugated.) In this manner, the complex vector AC(1:33) is constructed.

i. COMPUTE VELOCITY AT EACH DEPTH (P3): STEP 2. Now that the first lag autocorrelation has been calculated at each depth, the phase at each depth is the value to extract because it is directly proportional to the detected velocity at that depth. Specifically, for each autocorrelation value, a four quadrant arctangent lookup is used to determine the phase of the complex value. VELOC(k)=arc tan (imag(AC(k)), real(AC(k))). Each VELOC(k) value is proportional to the mean flow velocity at the gate depth k.

j. COMPUTE POWER AT EACH DEPTH (P3). The zeroth lag of the autocorrelation is calculated to obtain the Doppler signal power at each depth. The above velocity values and this set of power values over depth are the primary inputs to the embolus detection algorithm. Specifically, compute the signal power for each of the 4 ms period defined above. The computation of signal power will be done at each gate depth, yielding the vector POWER, each having 33 values. For the kth gate depth, again let P=Hr(k,1:M)+jHi(k,1:M). The resulting power values for this depth are POWER(k)=<P(1:M),P(1:M)> (note that in a dot product of complex values, the second vector is conjugated). In this manner, construct the real vector POWER(1:33).

k. LOG COMPRESS POWER (P3). The calculated power is converted to Decibels so that large and small signals can be observed together on a scale of reasonable size. Specifically, convert POWER to Decibels: POWERd(1:33)= 10*log 10(POWERd(1:33)).

2. Embolus Detection Part 1: Variable Definitions and Removal of Non-Transient Signals a. The following are constants and static arrays in the computer environment which will be modified for embolus detection based on power and velocity data (P4):

Constants:

AWINDOW 50, 50*4=200 ms buffer length. Must be even integer.

EWINDOW 20, 20*4=80 ms buffer length. Must be even integer.

FCLUTTER, 0.05*3.1415926, Clutter cutoff where nyquist=pi.

ABSTHRESH 100. Threshold for an artifact.

DBTHRESH 6.0. Threshold for including data in parabolic fit.

EMARGIN 25. Allowed margin between signatures for same embolus (25*4=100 ms).

AMARGIN 50. Allowed margin between signatures for same artifact.

POWER_THRESH 40. Threshold for integrated power under parabolic fit region in order to flag candidate embolic event.

CLUT_THRESH 27. Number of m-mode positions for which clutter velocity is not exceeded, at which embolus detection is temporarily disabled.

Ngates=33.

Arrays:

Msum[1 . . . EWINDOW],—each value is the sum of the absolute, background subtracted, decluttered power for a particular m-mode line.

Mwork[1 . . . EWINDOW],—utility array, 80 ms history

ClutCount,—number of values in the current m-mode line whose velocity falls below the clutter velocity threshold CLUT_THRESH MEPosition[1 . . . EWINDOW],—each value is the position of an embolus for a particular m-mode line MPLocal[1 . . . EWINDOW],—each value is the power in the vicinity of an embolus for a particular m-mode line MQ[1 . . . EWINDOW],—each value is the position of an embolus for an m-mode line, and has the status of "embolus candidate signal"

DELTA[1 . . . ngates],—each value is the delta follower of signal power at the given gate depth.

MsumA[1 . . . AWINDOW],—each value is the sum of the previous EWINDOW values in the Msum array. This value rises dramatically in the presence of an artifact signal.

b. Removing relatively constant signals (P4) consists of tracking the background power level at each depth and subtracting it from the currently observed power at each depth. The output of the subtraction is stored to a separated buffer and becomes the primary data buffer for performing embolus detection. Specifically, delta-follow the Decibel power traces at each depth and, at the same time, create the background subtracted vector SIGMA(k), where gate depth is indexed by k=1:33:

IF POWERd(k)>DELTA(k)
    THEN DELTA(k)=DELTA(k)+0.1 dB
    ELSE if POWERd(k)<DELTA(k)
        THEN DELTA(k)=DELTA(k)−0.1 dB
SIGMA(k)=POWER(k)−DELTA(k).

3. Embolud Detection Part 2: Removal of Clutter Signals (P4)

a. Clutter removal makes use of the fact when clutter occurs, it tends to appear as very low average velocity. In the spectrogram, clutter may have a vertical streak high intensity quality (broad band) that is intuitively seen as having zero mean velocity (i.e., zero mean Doppler shift frequency). Since the first lag autocorrelation method to calculate velocity results in mean velocity, then a clutter rejection plan is to zero out the power level anywhere in the m-mode line where the velocity falls below a threshold. Specifically, the set of 4 ms power and velocity data is processed with the routine DeClutter: DeClutter(VELOC, SIGMA). This routine DeClutter(VELOC,sigma) performs the following operations:

i. Mwork[I]=abs(VELOC[I]), where I={1 . . . ngates}.

ii. ClutCount=number of cases for which Mwork[I] <FCLUTTER, where I={1 . . . ngates}.

iii. If Mwork[I]<FCLUTTER, then SIGMA[I]=0, where I={1 . . . ngates}.

4. Embolus Detection Part 3: Review Remaining Signals and Determine if Embolus is Present (P4)

a. After the above call to the decluttering algorithm, the following analysis is done to determine the presence of an embolus. First, assuming an embolus is present, calculate its position within the M-Mode line, and the associated power in the vicinity of the embolus. Review the data with a number of questions that are based on a priori understanding of an embolus moving in blood flow. Specifically, process the set of 4 ms data by calling the routine Detect: Detect (VELOC, SIGMA). This routine Detect(VELOC,sigma) performs the following operations on the above global variables:

i. Sum the absolute background-subtracted decluttered power. When this value exceeds a sustained period of time, an artifact is present. Specifically, Msum[Acounter]=sum (abs(sigma[I])), where I={1 . . . ngates}. Acounter is a circular buffer counter that has maximum value at AWINDOW, and will be incremented at the end of the detect routine.

ii. Determine the value and location of the maximum background-subtracted decluttered power in the m-mode line. Specifically, [Y,Imax]=max(sigma[J]), where J={1 . . . ngates}. That is, Y is the maximum value of the buffer sigma, and is located at index Imax.

iii. Starting at the location of the maximum power, move towards a shallower depth and determine where the background-subtracted decluttered power falls below 6 dB. This sets one boundary for integrating the power in the vicinity of the hypothetical embolic signal. Specifically, starting at Imax-1 and moving in the shallower depth direction along the array sigma[1 . . . Imax−1], determine IShallow=index where sigma[index] falls below 6 dB.

iv. Starting at the location of the maximum power, move towards deep depth and determine where the background-subtracted decluttered power falls below 6 dB. This sets a second boundary for integrating the power in the vicinity of the hypothetical embolic signal. Specifically, starting at Imax+1 and moving in the deeper depth direction along the array sigma[Imax+1 . . . ngates], determine IDeep=index where sigma[index] falls below 6 db.

v. Fit a parabola to the power data between the 6 db points to determine a more accurate position of the peak power. Specifically, with the npts=Ideep-Ishallow+1 values in the array sigma[ ], determine the best parabolic fit coefficients [MP2,MP1.MP0] (least squared error), where MP2 is the second order coefficient.

vi. Using the parabolic fit coefficients, calculate the more accurate position of the maximum of the background subtracted decluttered power in the given m-mode line. This becomes the best guess for an embolus position, if an embolus is present. Specifically, MEPosition[Ecounter]= 28+2*IShallow−MP1/MP2. A cofactor of 2 is used because each gate increment corresponds to 2 mm depth change. Default MEPosition[Ecounter]=BUST=0 if MP2=0 or if npts of the parabolic fit is less than 3. Ecounter is a circular buffer counter that has max value at EWINDOW, and will be incremented at the end of the detect routine.

vii. Integrate the background subtracted decluttered power of the m-mode line within the 6 db points of the peak. This results in a "local power" that will be used in discriminating an embolus, which tends to have high localized power, from background blood flow. Specifically, MPLocal [Ecounter]=sum(sigma[j]) where j={Ishallow . . . Ideep}.

viii. Lay some additional ground work for separating an embolic signal from an artifact such as a probe or patient motion. This is done by looking at the history of the integrated absolute background subtracted decluttered power in each m-mode line, and seeing if it shows a sustained increase. Specifically, determine the median value of the previous 50 (200 ms) values of Msum[ ] array. This is a measure used in determining an artifact presence, i.e., if a substantial energy fluctuation lasts for an unusually long period of time. Normally, embolic signals are transients that last tens of milliseconds in the cerebral arteries. The median value is achieved by taking the median of the entire Msum array, since it is by design 200 ms in length (50 values). MsumA[Acounter]=median(Msum).

ix. Perform a series of binary tests to determine if an embolic event is occurring. If the outcome of these tests is TRUE, then the embolus position will be written to the MQ [ ] array. Specifically, start by setting MQ[Ecounter]=0. For ease of reference to older values in the circular buffer, assign Tminus1=Ecounter−1, Tminus2=Ecounter−2, Tminus3= Ecounter−3, and Tminus4=Ecounter−4. If any of these utility values is 0 or less, then wrap to the other end of the buffer: if TminusXX<=0 then TminusXX=TminusXX+ EWINDOW. Also, default test outcomes to negative before doing test: T0=T1=T2=T3=T4=T5=T6=T7=T8=0.

01. TEST1: Is there a large fluctuation in background power, which is consistent with an embolus? Specifically, if MPLocal[Ecounter]>POWER_THRESH then T0=1.

02. TEST2: In the present time period of 4 ms, is the embolus migrating at a speed consistent with very high-end blood flow velocity (2 m/s)? Specifically, if abs(MEPosition [Ecounter]−MEPosition[Tminus1])<4 millimeters then T1=1.

03. TEST3: In the penultimate time period of 4 ms, is the embolus migrating at a speed consistent with very high-end blood flow velocity (2 m/s)? Specifically, if abs(MEPosition [Tminus1]−MEPosition[Tminus2])<4 mm then T2=1. (Embolus traveling less than 2 m/s, during previous time period.)

04. TEST4: Does the parabolic fit for the current time period show the embolus position to not closer than 5 mm to either display edge? Specifically, if MEPosition [Ecounter]>27 mm and MEPosition[Ecounter]<81 mm then T3=1.

05. TEST5: Does the parabolic fit for the previous time period show the embolus position to not closer than 5 mm to either display edge? Specifically, if MEPosition[Tminus1] >27 mm and MEPosition[Tminus1]<81 mm then T4=1.

06. TEST6: Does the parabolic fit for two time periods ago show the embolus position to not closer than 5 mm to either display edge? Specifically, if MEPosition[Tminus2] >27 mm and MEPosition[Tminus2]<81 mm then T5=1.

07. TEST7: Does the parabolic fit for three time periods ago show the embolus position to not closer than 5 mm to either display edge? Specifically, if MEPosition[Tminus3] >27 mm and MEPosition[Tminus3]<81 mm then T8=1.

08. TEST8: Does the embolus show uniform direction of motion away from the transducer in the current and previous two time periods? Specifically, if (MEPosition[Tminus2]<= MEPosition[Tminus1]) AND (MEPosition[Tminus1]<= MEPosition[Ecounter]) then T6=1.

09. TEST9: Does the embolus show uniform direction of motion towards the transducer in the current and the previous time periods? Specifically, if (MEPosition[Tminus2]>= MFPosition[Tminus1 ]) AND (MEPosition[Tminus1 ]>=MEPosition[Ecounter]) then T7=1.

10. If (Test1=TRUE and Test2=TRUE and Test3=TRUE and Test4=TRUE and Test5=TRUE and Test8=TRUE and (Test6=TRUE or Test7=TRUE), then the candidate event is considered embolic. Specifically, if (T0=1 AND T1=1 AND T2=1 AND T3=1 AND T4=1 AND T5=1 AND T8=1 AND (T6=1 OR T7=1)) THEN {MQ[Ecounter]=MEPosition [Ecounter], MQ[Tminus1]=MEPosition[Tminus1], AND MQ[Tminus2]=MEPosition[Tminus2]}.

x. Review the results of the above calculations and tests with the larger perspective of whether an artifact signal has been identified and needs to preclude positive embolus detection results, OR whether the embolic signal is on-going and processing should be completed in a timely manner before the host system is informed that an embolus has passed through the beam. Specifically, the goal of this section is to determine whether to set Edetect or Adetect, respectively telling the host whether and embolus or artifact has occurred.

01. FIRST REVIEW DATA FOR ARTIFACT STATUS. Preclude an embolus from being flagged if the artifact status is ongoing or an artifact interrupts an embolic signal. Specifically, the two primary factors that determine if an artifact signal has been detected are if the MsumA long term energy detector has exceeded a threshold, or if an abnormal number of signals have resulted in very low velocity (this happens when the probe or the patient is physically tapped or bumped):

```
if (MSumA[ACounter]>ABSTHRESH OR
   ClutCount>CLUT_THRESH) THEN
{
  If this artifact detection is a new artifact, then set
  the appropriate flags to initial values.
  if (AFlag=FALSE)
  {
    EFlag=FALSE Override any embolus detection
    AFlag=TRUE Initiate artifact designation
  }
  ADownCount=0 Initialize "Post-artifact" margin
    counter
}
``` else {If we reach this point, artifact signal is gone.
    Are we in the margin immediately after an artifact?
    if (AFlag==TRUE AND ADownCount<AMARGIN)
    {
        Bump up margin counter
        ADownCount=ADownCount+1
    }
    else {if we reach this point, artifact is gone and
    margin after artifact has been completed.
        if (AFlag==TRUE) {
            AFlag=FALSE Turn off artifact flag.
            Tell the host we've seen an artifact, don't reset
            this flag message has been sent to host.
            ADetect=TRUE
        }
    }
}
02. SECOND REVIEW DATA FOR EMBOLUS STATUS IF an artifact does not preclude flagging an embolus, then the evidence is reviewed to determine whether to flag the event as embolic. Specifically, the primary indicators for an embolus is if the MQ[Ecounter] has been set to a valid depth (non-zero, between 27 and 81 mm) AND an artifact is not in progress (Aflag false). The latter requirement has been reviewed in the section immediately above, so an artifact in progress will disable an existing embolic event (above) and preclude further declaration of an embolic event (below):

if (MQ[ECounter]>0 AND AFlag==FALSE) {
        If an embolic event is new, then initialize
        appropriate values.
        if (EFlag==FALSE) {
            EFlag=TRUE Declare embolic event in
            progress.
        }
        While an embolic event is in progress, zero the
        length of the post-embolus margin counter.
        EDownCount=0
    }
    else {If we reach this point, the embolic event has
    completed and we need to delay further detection for
    the post-embolic margin of 100 ms (EMARGIN).
        if (EFlag==TRUE AND EDownCount<EMARGIN)
        }
        Bump up margin counter.
        EDownCount=EDownCount+1
    }
    else {If we reach this point, embolus is gone and
    margin after embolus has been completed.
        if (EFlag==TRUE) {
            EFlag=FALSE Turn off embolic event flag.
            Tell the host we've seen an artifact, don't reset
            this flag message has been sent to host.
            EDetect=TRUE
        }
    }
}
03. Adjust Increment Acounter and Ecounter by one. If Acounter exceeds AWINDOW then reset Acounter to 1. If Ecounter exceeds EWINDOW then reset Ecounter to 1.

04. Update embolus counter for user and mark the display appropriately.

Those skilled in the art will appreciate that the invention may be accomplished with circuits other than those particularly depicted and described in connection with FIGS. 9–11. These figures represent just one of many possible implementations of a Doppler ultrasound system in accordance with the invention. Likewise, the invention may be accomplished using process steps other than those particularly depicted and described in connection with FIG. 12–18.

Moreover, it will be appreciated that effective embolus detection may be achieved using an embolus detection method including less than all four algorithm parts, as was previously mentioned. For example, embolus detection may be achieved by implementing an embolus detection algorithm that removes from the data compiled by the Doppler system non-transient signals that present relatively constant Doppler power at each gate depth and then conducts a battery of binary characterization tests to determine whether the remaining data is consistent with the behavior of an embolic event. Although less than the four algorithm parts are used in the detection algorithm, embolus detection may still be made. The accuracy of the detection method may be affected by such a detection algorithm. However, the effect on the accuracy may not be so great as to compromise the overall effectiveness of the embolus detection algorithm, but will have the advantage of reducing processing time or the complexity of the detection algorithm is desired. Therefore, it will be appreciated that detection algorithms having more or less than the four algorithm parts previously described remain within the scope of the present invention.

Although the detection algorithm has been described with respect to embodiments of automated embolus detection, alternatively, embolus detection may be made by applying some or all of the algorithms previously described, displaying the resulting information on a display device and having a user visually detect the occurrence of an embolic event. Methods of visually detecting embolic events may be made with the assistance of embodiments of the Doppler ultrasound system previously described. However, it will be appreciated that embodiments of the embolus detection method are not limited to a particular Doppler ultrasound system, except to the extent recited by the appended claims.

Those skilled in the art will also understand that each of the circuits whose functions and interconnections are described in connection with FIGS. 9–11 is of a type known in the art. Therefore, one skilled in the art will be readily able to adapt such circuits in the described combination to practice the invention. Particular details of these circuits are not critical to the invention, and a detailed description of the internal circuit operation need not be provided. Similarly, each one of the process steps described in connection with FIGS. 12–18 will be understood by those skilled in the art, and may itself be a sequence of operations that need not be described in detail in order for one skilled in the art to practice the invention.

It will be appreciated that, although specific embodiments of the invention have been described for purposes of illustration, various modifications may be made without deviating from the spirit and scope of the invention. For example, a user interface in accordance with the present invention may be provided by means other than a video display, such as a printer or other visual display device. Those skilled in the art will also appreciate that many of the advantages associated with these circuits and processes described above may be provided by other circuit configurations and processes. Accordingly, the invention is not limited by the particular disclosure above, but instead the scope of the invention is determined by the following claims.

What is claimed is:

1. A method for detecting embolic events in a Doppler ultrasound system sensing motion along an ultrasound beam, the method comprising:

compiling movement information for a plurality of locations along the ultrasound beam, the movement information including detected Doppler shift signal power and associated velocity for a length of time having a plurality of time periods; and determining the occurrence of an embolic event from the compiled movement information for each of the time periods.

2. The method of claim 1 wherein determining the occurrence of an embolic event comprises:

subtracting a respective background power level from the compiled movement information for each of the plurality of locations; and performing a plurality of binary characterization tests to determine whether the resultant compiled movement information is indicative of an embolic event.

3. The method of claim 2 wherein the plurality of binary characterization tests comprises identifying from the resultant compiled movement information the position of the embolic event.

4. The method of claim 3, further comprising determining whether the position of the embolic event occurs between a first depth and a second depth.

5. The method of claim 3 wherein identifying the position of the embolic event comprises locating the depth of maximum detected power along the ultrasound beam.

6. The method of claim 2 wherein the plurality of binary characterization tests includes determining whether the resultant compiled movement information is indicative of an embolic event having a velocity not exceeding a high-end blood flow velocity.

7. The method of claim 6 wherein the high-end blood flow velocity is approximately 2 meters per second.

8. The method of claim 2 wherein the plurality of binary characterization tests includes determining whether the resultant compiled movement information is indicative of an embolic event having uniform motion away from or towards the source of the ultrasound beam for a minimum number of time intervals.

9. The method of claim 2 wherein the plurality of binary characterization tests includes determining whether the resultant compiled movement information of a potential embolic event has sufficient power fluctuation from the background power level.

10. The method of claim 1, further comprising displaying the compiled movement information for observation by a user.

11. The method of claim 10 wherein determining the occurrence of an embolic event is made visually by the user.

12. A method for detecting embolic events in a Doppler ultrasound system sensing motion along an ultrasound beam, the method comprising:

compiling for a plurality of time periods movement information for a plurality of locations along the ultrasound beam, the movement information including detected Doppler shift signal power and associated velocity;

subtracting a respective background power level from the compiled movement information for each time period and each of the plurality of locations;

displaying the resultant compiled movement information on a display device; and visually determining from the displayed complied movement information the occurrence of an embolic event.

13. The method of claim 12 wherein displaying the resultant compiled movement information comprises displaying the resultant compiled movement information along time, position and power axes.

14. The method of claim 13 wherein visually determining the occurrence of an embolic event comprises identifying the position of the embolic event.

15. The method of claim 14, further comprising determining whether the position of the embolic event occurs between a first depth and a second depth.

16. The method of claim 14 wherein identifying the position of the embolic event comprises locating the depth of maximum detected power along the ultrasound beam for at least one time period.

17. The method of claim 13 wherein visually determining the occurrence of an embolic event comprises determining whether the velocity of the embolic event does not exceed a high-end blood flow velocity.

18. The method of claim 17 wherein the high-end blood flow velocity is approximately 2 meters per second.

19. The method of claim 13 wherein visually determining the occurrence of an embolic event comprises determining whether the embolic event has uniform motion away from or towards the source of the ultrasound beam for a time interval.

20. The method of claim 13 wherein visually determining the occurrence of an embolic event comprises determining whether the embolic event has sufficient power fluctuation from the background power level.

21. A method for detecting embolic events in a Doppler ultrasound system sensing motion along an ultrasound beam, the method comprising:

compiling for a plurality of time periods movement information for a plurality of locations along the ultrasound beam, the movement information including detected Doppler shift signal power and associated velocity;

for each time period, removing movement information having a detected velocity less than a velocity threshold from the compiled movement information; and displaying on a display device the resultant compiled movement information along time and position axes; and visually determining from the displayed resultant complied movement information the occurrence of an embolic event.

22. The method of claim 21 wherein visually determining the occurrence of an embolic event comprises identifying the position of the embolic event.

23. The method of claim 22, further comprising determining whether the position of the embolic event occurs between a first depth and a second depth.

24. The method of claim 21 wherein visually determining the occurrence of an embolic event comprises determining whether the velocity of the embolic event does not exceed a high-end blood flow velocity.

25. The method of claim 24 wherein the high-end blood flow velocity is approximately 2 meters per second.

26. The method of claim 21 wherein visually determining the occurrence of an embolic event comprises determining whether the embolic event has uniform motion away from or towards the source of the ultrasound beam for a time interval.

27. A method for detecting embolic events in a Doppler ultrasound system sensing motion along an ultrasound beam, the Doppler ultrasound system compiling for a plurality of time periods movement information including detected Doppler shift signal power and associated velocity for a plurality of locations along the ultrasound beam, the method comprising:

removing from the compiled movement information for each time period movement information having a detected velocity less than a velocity threshold; and performing for each time period a plurality of binary characterization tests to determine whether the resultant compiled movement information is indicative of an embolic event.

28. The method of claim 27 wherein the velocity threshold is approximately equal to 7 cm/s.

29. The method of claim 27 wherein the plurality of binary characterization tests comprises identifying from the resultant compiled movement information the position of the embolic event.

30. The method of claim 29, further comprising determining whether the position of the embolic event occurs between a first depth and a second depth.

31. The method of claim 29 wherein identifying the position of the embolic event comprises locating the maximum detected ultrasound power along the ultrasound beam.

32. The method of claim 27 wherein the plurality of binary characterization tests includes determining whether the resultant compiled movement information is indicative of an embolic event having a velocity not exceeding a high-end blood flow velocity.

33. The method of claim 32 wherein the high-end blood flow velocity is approximately 2 meters per second.

34. The method of claim 27 wherein the plurality of binary characterization tests includes determining whether the resultant compiled movement information is indicative of an embolic event having uniform motion away from or towards the source of the ultrasound beam for a minimum number of time intervals.

35. The method of claim 27 wherein the plurality of binary characterization tests includes determining whether the resultant compiled movement information of a potential embolic event has sufficient power fluctuation from the background power level.

36. The method of claim 27, further comprising displaying the compiled movement information for observation by a user.

37. The method of claim 27, further comprising reviewing the results of the binary characterization tests and rejecting false positive identification of an embolic event.

38. The method of claim 37, further comprising automatically incrementing a counter when it is determined that the resultant compiled movement information is consistent with the characteristics of an embolic event.

39. A method for detecting embolic events in a Doppler ultrasound system sensing motion along an ultrasound beam, the Doppler ultrasound system compiling for a plurality of time periods movement information including detected Doppler shift signal power and associated velocity for a plurality of locations along the ultrasound beam, the method comprising:

subtracting a respective background power level from the compiled movement information for each time period and each of the plurality of locations;

for each time period, removing movement information having a detected velocity less than a velocity threshold from the subtracted compiled movement information; and performing a plurality of binary characterization tests for each time period to determine whether the resultant compiled movement information is consistent with the occurrence of an embolic event.

40. The method of claim 39 wherein the velocity threshold is approximately equal to 7 cm/s.

41. The method of claim 39 wherein the plurality of binary characterization tests comprises identifying from the resultant compiled movement information the position of the embolic event.

42. The method of claim 41, further comprising determining whether the position of the embolic event occurs between a first depth and a second depth.

43. The method of claim 41 wherein identifying the position of the embolic event comprises locating the maximum detected ultrasound power along the ultrasound beam.

44. The method of claim 39 wherein the plurality of binary characterization tests includes determining whether the resultant compiled movement information is indicative of an embolic event having a velocity not exceeding a high-end blood flow velocity.

45. The method of claim 44 wherein the high-end blood flow velocity is approximately 2 meters per second.

46. The method of claim 39 wherein the plurality of binary characterization tests includes determining whether the resultant compiled movement information is indicative of an embolic event having uniform motion away from or towards the source of the ultrasound beam for a minimum number of time intervals.

47. The method of claim 39 wherein the plurality of binary characterization tests includes determining whether the resultant compiled movement information of a potential embolic event has sufficient power fluctuation from the background power level.

48. The method of claim 39, further comprising displaying the compiled movement information for observation by a user.

49. The method of claim 39, further comprising reviewing the results of the binary characterization tests and rejecting false positive identification of an embolic event.

50. The method of claim 39, further comprising automatically incrementing a counter when it is determined that the resultant compiled movement information is consistent with the characteristics of an embolic event.

51. A method for detecting embolic events in a Doppler ultrasound system sensing motion along an ultrasound beam, the Doppler ultrasound system compiling for a plurality of time periods movement information including detected Doppler shift signal power and associated velocity for a plurality of locations along the ultrasound beam, the method comprising:

performing for each time period a plurality of binary characterization tests indicative of embolic events on the compiled movement information to identify the occurrence of an embolic event; and rejecting false positive embolic events.

52. The method of claim 51 wherein performing the plurality of binary characterization tests comprises identifying from the compiled movement information the position of the embolic event.

53. The method of claim 52, further comprising determining whether the position of the embolic event occurs between a first depth and a second depth.

54. The method of claim 52 wherein identifying the position of the embolic event comprises locating the maximum detected ultrasound power along the ultrasound beam.

55. The method of claim 51 wherein the plurality of binary characterization tests includes determining whether the compiled movement information is indicative of an embolic event having a velocity not exceeding a high-end blood flow velocity.

56. The method of claim 55 wherein the high-end blood flow velocity is approximately 2 meters per second.

57. The method of claim 51 wherein the plurality of binary characterization tests includes determining whether the compiled movement information is indicative of an embolic event having uniform motion away from or towards the source of the ultrasound beam for a minimum number of time intervals.

58. The method of claim 51 wherein the plurality of binary characterization tests includes determining whether the compiled movement information of a potential embolic event has sufficient power fluctuation from the background power level.

59. The method of claim 51, further comprising displaying the compiled movement information for observation by a user.

60. The method of claim 51, further comprising automatically incrementing a counter when it is determined that the compiled remaining movement information is consistent with the characteristics of an embolic event.

61. A method for detecting embolic events in a Doppler ultrasound system sensing motion along an ultrasound beam, the Doppler ultrasound system compiling for a plurality of time periods movement information including detected Doppler shift signal power and associated velocity for a plurality of locations along the ultrasound beam, the method comprising:

subtracting a respective background power level from the compiled movement information for each time period and each of the plurality of locations;

performing for each time period a plurality of binary characterization tests indicative of embolic events on the resultant compiled movement information to identify the occurrence of an embolic event; and rejecting false positive embolic events.

62. The method of claim 61 wherein performing the plurality of binary characterization tests comprises identifying from the resultant compiled movement information the position of the embolic event.

63. The method of claim 62, further comprising determining whether the position of the embolic event occurs between a first depth and a second depth.

64. The method of claim 62 wherein identifying the position of the embolic event comprises locating the maximum detected ultrasound power along the ultrasound beam.

65. The method of claim 61 wherein the plurality of binary characterization tests includes determining whether the resultant compiled movement information is indicative of an embolic event having a velocity not exceeding a high-end blood flow velocity.

66. The method of claim 65 wherein the high-end blood flow velocity is approximately 2 meters per second.

67. The method of claim 61 wherein the plurality of binary characterization tests includes determining whether the resultant compiled movement information is indicative of an embolic event having uniform motion away from or towards the source of the ultrasound beam for a minimum number of time intervals.

68. The method of claim 61 wherein the plurality of binary characterization tests includes determining whether the resultant compiled movement information of a potential embolic event has sufficient power fluctuation from the background power level.

69. The method of claim 61, further comprising displaying the resultant compiled movement information for observation by a user.

70. The method of claim 61, further comprising automatically incrementing a counter when it is determined that the resultant compiled movement information is consistent with the characteristics of an embolic event.

71. A Doppler ultrasound system for sensing motion along an ultrasound beam and detecting embolic events, the system comprising:

an ultrasound transducer operable to detect ultrasound signals and responsively produce corresponding electrical signals;

signal processing circuitry coupled with the transducer to receive the electrical signals and compile for a plurality of time periods movement information including detected Doppler shift signal power and associated velocity for a plurality of locations along the ultrasound beam; and detection circuitry coupled to receive the compiled movement information from the signal processing circuitry and operable to perform a plurality of binary characterization tests for each time period to determine whether the compiled movement information is consistent with the occurrence of an embolic event.

72. The Doppler ultrasound system of claim 71 wherein the detection circuitry is further operable to subtract a respective background power level from the compiled detected Doppler ultrasound power for each of the plurality of locations and time period.

73. The Doppler ultrasound system of claim 72 wherein for each time period the detection circuitry is further operable to remove movement information having a detected velocity less than a velocity threshold from the subtracted compiled movement information.

74. The Doppler ultrasound system of claim 73 wherein the velocity threshold approximately equal to 7 cm/s.

75. The Doppler ultrasound system of claim 71 wherein the detection circuitry is further operable to review the results of the plurality of binary characterization tests and reject false positive identification of embolic events.

76. The Doppler ultrasound system of claim 71, further comprising a display device coupled to the signal processing circuitry and the detection circuitry to display the compiled movement information for a user.

77. The Doppler ultrasound system of claim 71 wherein the detection circuitry is further operable to count the number of events determined to be embolic.

78. The Doppler ultrasound system of claim 71 wherein the plurality of binary characterization tests comprises identifying the position of the embolic event by locating the maximum power for each of the plurality of locations along the ultrasound beam.

79. The system of claim 78 wherein the plurality of binary characterizations tests further comprises determining whether the position of the embolic event occurs between a first depth and a second depth.

80. The Doppler ultrasound system of claim 71 wherein the plurality of binary characterization tests comprises determining whether the compiled movement information is consistent with an embolic event having a velocity not exceeding a high-end blood flow velocity.

81. The Doppler ultrasound system of claim 80 wherein the high-end blood flow velocity is approximately 2 meters per second.

82. The Doppler ultrasound system of claim 71 wherein the plurality of binary characterization tests comprises determining whether the compiled movement information is indicative of an embolic event having uniform motion away from or towards the ultrasound transducer for a minimum number of time intervals.

83. The Doppler ultrasound system of claim 71 wherein the plurality of binary characterization tests comprises determining whether the compiled movement information of a potential embolic event has sufficient power fluctuation from the background power level.

84. A computer-readable medium having a computer executable program for detecting embolic events, the computer program comprising instructions, which when executed by a Doppler ultrasound system sensing motion along an ultrasound beam perform the steps of:
   compiling for a plurality of time periods movement information for a plurality of locations along the ultrasound beam, the movement information including detected Doppler shift signal power and associated velocity; and
   performing a plurality of binary characterization tests for each time period to determine whether the compiled movement information is indicative of the occurrence of an embolic event.

85. The computer readable medium of claim 84, further comprising subtracting a respective background power level from the compiled detected Doppler ultrasound power for each of the plurality of locations and time periods.

86. The computer readable medium of claim 85, further comprising removing movement information having a detected velocity less than a velocity threshold from the subtracted compiled movement information for each time period.

87. The computer readable medium of claim 86 wherein the velocity threshold approximately equal to 7 cm/s.

88. The computer readable medium of claim 84, further comprising reviewing the results of the binary characterization tests and rejecting false positive identification of embolic events.

89. The computer readable medium of claim 84 wherein the plurality of binary characterization tests comprises identifying from the compiled movement information the position of the embolic event.

90. The computer readable medium of claim 89 wherein the plurality of binary characterization tests further comprises determining whether the position of the embolic event occurs between a first depth and a second depth.

91. The computer readable medium of claim 89 wherein identifying the position of the embolic event comprises locating the depth of maximum detected power along the ultrasound beam for a plurality of time segments.

92. The computer readable medium of claim 84 wherein the plurality of binary characterization tests includes determining whether the compiled movement information is consistent with an embolic event having a velocity not exceeding a high-end blood flow velocity.

93. The computer readable medium of claim 92 wherein the high-end blood flow velocity comprises approximately 2 meters per second.

94. The computer readable medium of claim 84 wherein the plurality of binary characterization tests includes determining whether the compiled movement information is indicative of an embolic event having uniform motion away from or towards the source of the ultrasound beam for a minimum number of time intervals.

95. The computer readable medium of claim 84 wherein the plurality of binary characterization tests includes determining whether the compiled movement information of a potential embolic event has sufficient power fluctuation from the background power level.

96. The computer readable medium of claim 84, further comprising displaying the compiled movement information for observation by a user.

97. The computer readable medium of claim 84, further comprising automatically incrementing a counter when it is determined that the compiled movement information is indicative of the occurrence of an embolic event.

* * * * *

UNITED STATES PATENT AND TRADEMARK OFFICE
CERTIFICATE OF CORRECTION

PATENT NO. : 6,524,249 B2
DATED : February 25, 2003
INVENTOR(S) : Mark A. Moehring and Timothy R. Myers It is certified that error appears in the above-identified patent and that said Letters Patent is hereby corrected as shown below:

Title page,
Item [56], References Cited, OTHER PUBLICATIONS, "Omoto" reference (second reference, reads "et al., Clinical Significance and Prospects of 'Real-Time Two-Dimensional Doppler Echocardiography'," should read -- et al., "Clinical Significance and Prospects of "Real-Time Two-Dimensional Doppler Echocardiography,"" --
"Aloka" reference (first reference), reads "and above. pp. i-15-2" should read -- and above, pp. i-15-2 --

Column 1,
Line 43, reads "And Apparatus For" should read -- and Apparatus for --

Column 5,
Line 40, reads "beat; (2)the blue" should read -- beat; (2) the blue --

Column 6,
Line 28, reads "consequently no there" should read -- consequently there --

Column 10,
Line 15, reads "determined by a creating," should read -- determined by creating, --
Line 31, reads "as a means to decimating" should read -- as a means of decimating --

Column 11,
Line 42, reads "value, us a four quadrant" should read -- value, use a four quadrant --

Column 14,
Line 28, reads "POWERdS, Pd5," should read -- POWERd5, Pd5, --
Line 46, reads "mm=c*T1/2, where" should read -- mm=c*T1/2, where --

Column 16,
Line 6, reads "in this regard? and (2)" should read -- in this regard?) and (2) --
Line 8, reads "either toward, or away from" should read -- either toward or away from --

Column 19,
Line 3, reads "period defined above." should read -- periods defined above. --

Column 20,
Line 13, reads "Embolud Detection Part 2:" should read -- Embolus Detection Part 2: --

UNITED STATES PATENT AND TRADEMARK OFFICE
CERTIFICATE OF CORRECTION

PATENT NO. : 6,524,249 B2
DATED : February 25, 2003
INVENTOR(S) : Mark A. Moehring and Timothy R. Myers It is certified that error appears in the above-identified patent and that said Letters Patent is hereby corrected as shown below:

Column 21,
Line 6, reads "falls below 6 db." should read -- falls below 6 dB. --
Line 7, reads "between the 6 db points" should read -- between the 6 dB points --
Line 10, reads "[MP2, MP1.MP0]" should read -- [MP2, MP1, MP0] --
Line 24, reads "within the 6 db points" should read -- within the 6 dB points --

Column 22,
Line 26, reads "MFPosition[Tminus1 ])" should read -- MFPosition[Tminus1]) --
Line 44, reads "host whether and embolus" should read -- host whether an embolus --

Column 24,
Line 3, reads "with FIG. 12-18." should read -- with FIGS. 12-18. --
Line 21, reads "algorithm is desired." should read -- algorithm if desired. --

Column 30,
Line 30, reads "threshold approximately" should read -- threshold is approximately --
Line 48, reads "characterizations tests" should read -- characterization tests --

Column 31,
Line 27, reads "threshold approximately" should read -- threshold is approximately --

Signed and Sealed this

Nineteenth Day of October, 2004

JON W. DUDAS
*Director of the United States Patent and Trademark Office*

UNITED STATES PATENT AND TRADEMARK OFFICE
CERTIFICATE OF CORRECTION

PATENT NO.     : 6,524,249 B2
DATED          : February 25, 2003
INVENTOR(S)    : Mark A. Moehring and Timothy R. Myers It is certified that error appears in the above-identified patent and that said Letters Patent is hereby corrected as shown below:

Title page,
Item [56], References Cited, OTHER PUBLICATIONS, "Omoto" reference (second reference, reads "et al., Clinical Significance and Prospects of 'Real-Time Two-Dimensional Doppler Echocardiography'," should read -- et al., "Clinical Significance and Prospects of "Real-Time Two-Dimensional Doppler Echocardiography,'" --.
"Aloka" reference (first reference), reads "and above. pp. i-15-2" should read -- and above, pp. i-15-2 --.

Column 1,
Line 43, reads "And Apparatus For" should read -- and Apparatus for --.

Column 5,
Line 40, reads "beat; (2)the blue" should read -- beat; (2) the blue --.

Column 6,
Line 28, reads "consequently no there" should read -- consequently there --.
Line 54, reads "depthmode display 102" should read -- depth-mode display 102 --.

Column 10,
Line 15, reads "determined by a creating," should read -- determined by creating, --.
Line 31, reads "as a means to decimating" should read -- as a means of decimating --.

Column 11,
Line 42, reads "value, us a four quadrant" should read -- value, use a four quadrant --.

Column 14,
Line 28, reads "POWERdS, Pd5," should read -- POWERd5, Pd5, --.
Line 46, reads "mm=c*T1/2, where" should read -- mm=c*T1/2, where --.

Column 16,
Line 6, reads "in this regard? and (2)" should read -- in this regard?) and (2) --.
Line 8, reads "either toward, or away from" should read -- either toward or away from --.

Column 19,
Line 3, reads "period defined above." should read -- periods defined above. --.

Column 20,
Line 13, reads "Embolud Detection Part 2:" should read -- Embolus Detection Part 2: --.

UNITED STATES PATENT AND TRADEMARK OFFICE
CERTIFICATE OF CORRECTION

PATENT NO. : 6,524,249 B2
DATED : February 25, 2003
INVENTOR(S) : Mark A. Moehring and Timothy R. Myers It is certified that error appears in the above-identified patent and that said Letters Patent is hereby corrected as shown below:

Column 21,
Line 6, reads "falls below 6 db." should read -- falls below 6 dB. --.
Line 7, reads "between the 6 db points" should read -- between the 6 dB points --.
Line 10, reads "[MP2, MP1.MP0]" should read -- [MP2, MP1, MP0] --.
Line 24, reads "within the 6 db points" should read -- within the 6 dB points --.

Column 22,
Line 26, reads "MFPosition[Tminus1 ])" should read -- MFPosition[Tminus1]) --.
Line 44, reads "host whether and embolus" should read -- host whether an embolus --.

Column 24,
Line 3, reads "with FIG. 12-18." should read -- with FIGS. 12-18. --.
Line 21, reads "algorithm is desired." should read -- algorithm if desired. --.

Column 30,
Line 30, reads "threshold approximately" should read -- threshold is approximately --.
Line 48, reads "characterizations tests" should read -- characterization tests --.

Column 31,
Line 27, reads "threshold approximately" should read -- threshold is approximately --.

This certificate supersedes Certificate of Correction issued October 19, 2004.

Signed and Sealed this

Thirteenth Day of December, 2005

JON W. DUDAS
*Director of the United States Patent and Trademark Office*